(12) United States Patent
Miller

(10) Patent No.: US 7,112,661 B1
(45) Date of Patent: Sep. 26, 2006

(54) VARIABLE HEAVY CHAIN AND VARIABLE LIGHT CHAIN REGIONS OF ANTIBODIES TO HUMAN PLATELET GLYCOPROTEIN IB ALPHA

(75) Inventor: Jonathan L. Miller, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/430,048

(22) Filed: Oct. 29, 1999

Related U.S. Application Data

(60) Provisional application No. 60/106,275, filed on Oct. 30, 1998.

(51) Int. Cl.
C07K 16/00 (2006.01)
C12P 21/08 (2006.01)
C12N 5/06 (2006.01)

(52) U.S. Cl. ............... 530/387.1; 530/387.3; 435/5; 435/320.1; 435/328; 435/334; 435/DIG. 22; 435/DIG. 35; 424/130.1; 424/133.1; 424/178.1

(58) Field of Classification Search .......... 435/5, 435/320.1, DIG. 22, DIG. 35, 328, 334; 530/387.1, 387.3; 424/130.1, 133.1, 178.1
See application file for complete search history.

(56) References Cited

U.S. PATENT DOCUMENTS

| | | | |
|---|---|---|---|
| 5,486,361 A | | 1/1996 | Gralnick |
| 5,817,748 A | * | 10/1998 | Miller et al. ............... 530/300 |
| 5,962,255 A | | 10/1999 | Griffiths et al. |
| 5,969,108 A | | 10/1999 | McCafferty et al. |
| 2003/0077613 A1 | * | 4/2003 | Soderlind et al. ............... 435/6 |

FOREIGN PATENT DOCUMENTS

| | | | |
|---|---|---|---|
| EP | 0 372 670 | | 6/1990 |
| WO | WO 92/14750 | | 9/1992 |
| WO | WO 93/16712 | | 9/1993 |
| WO | WO 96/17622 | | 6/1996 |
| WO | WO 97/18236 | | 5/1997 |
| WO | WO9832845 | * | 7/1998 |

OTHER PUBLICATIONS

Okamoto et al (Tissue Antigens, vol. 51, pp. 156-163, 1998.*
Miller et al (Arteriosclerosis and Thrombosis, vol. 11, No. 5, pp. 1231-1236, 1991).*
Schroeder et al (Proc. Natl. Acad. Sci. USA. vol. 87. p. 6146-6150, Aug. 1990).*
Raaphorst et al. (Eur. J. Immunol. 1992. vol. 22 . No. 1. pp. 247-251.*
Carter, "Binders from the deepest vaults", Nat Biotech 14(3):267 (1996).
Griffiths et al., "Isolation of high affinity human antibodies directly from large synthetic repertoires", EMBO J 13(14):3245-3260 (1994).
Hiraiwa et al., "Sequence Analysis of Monoclonal Antibodies Derived From A Patient With Idiopathic Thrombocytopenic Purpura", Autoimmunity 8:107-113 (1990).
Hoogenboom and Winter, "By-passing Immunisation. Human Antibodies from Synthetic Repertoires of Germline V(sub H) Gene Segments Rearranged in Vitro", 227:381-388 (1992).
Konkle et al., "Cytokine-enhanced Expression of Glycoprotein Ib alpha in Human Endothelium", J Biol Chem 265(32):19833-19838 (1990).
McCafferty et al., "Phage antibodies: filamentous phage displaying antibody variable domains", Nature 348:552-554 (1990).
Miller and Lyle, "Mimotope / anti-mimotope probing of structural relationship in platelet glycoprotein Ib alpha", Proc Natl Acad Sci USA 93:3565-3569 (1996).
Miller et al., "Selection of phagemid recognizing human platelet GPIb from a human V(sub H) and V(sub L) Immunoglobulin phagemid library", Blood 90(10), Abstract 3016 (Nov. 15, 1997).
Miller et al., "Isolation and Characterization of Single Chain Human Antibodies Directed Against Epitopes Within Human Platelet GPIb alpha", Blood 92(10), Abstract (Nov. 15, 1998).
Nissim et al., "Antibody fragments from a 'single pot' phage display library as immunochemical reagents", EMBO J 13(3):692-698 (1994).

(Continued)

*Primary Examiner*—Padmashri Ponnaluri
(74) *Attorney, Agent, or Firm*—Rogalskyj & Weyand, LLP

(57) ABSTRACT

The present invention is directed to a method of selecting a clone that binds to human platelet glycoprotein Ib alpha using a human variable heavy chain and variable light chain immunoglobulin library. The invention is further directed to isolated nucleic acid molecules encoding a variable heavy chain or variable light chain region of an antibody, wherein the antibody binds to human platelet glycoprotein Ib alpha and inhibits aggregation of platelets. Expression vectors and host cells comprising the nucleic acid molecules are also provided, as well as methods for producing the variable heavy chain or the variable light chain region. An isolated variable heavy chain or variable light chain region of an antibody, wherein the antibody binds to human platelet glycoprotein Ib alpha and inhibits aggregation of platelets, is also provided. An antibody comprising the variable heavy chain or variable light chain regions is provided, as is a composition comprising the antibody and a carrier. The subject invention further provides a method of inhibiting aggregation of platelets, as well as a method of binding human platelet glycoprotein Ib alpha. A method of selecting a variable heavy chain or variable light chain region of an antibody is also provided.

7 Claims, 12 Drawing Sheets

OTHER PUBLICATIONS

Sait, "The Human Synthetic VH+VL scFv Library / Agreement relating to the supply of The Human Synthetic VH+VL scFv Library / Protocol for use of the Human Synthetic VH+VL scFv Library", Medical Research Council Center for Protein Engineering website (http://ind1.mrc-lmb.cam.ac.uk/cpe-home-page.html)(1997).

Tomlinson, "V Base. Introduction / V Base. Sequence Alignments", Medical Research Council Center for Protein Engineering website (http://ind1.mrc-lmb.cam.ac.uk/cpe-home-page.html)(1997).

Tomlinson et al., "The Repertoire of Human Germline V(sub H) Sequences Reveals about Fifty Groups of V(sub H) Segments with Different Hypervariable Loops", J Mol Biol 227:776-798 (1992).

Vaughan et al., "Human Antibodies with Sub-nanomolar Affinities Isolated from a Large Non-immunized Phage Display Library", Nature Biotech 14:309-314 (1996).

Ware et al., J. Biol. Chem., 268(11):8376-8382(1993).

* cited by examiner

Hib-1

VH Exon - Amino acid sequence alignment

```
                         FR1                                CDR1           FR2              CDR2                    FR3
                1         2         3                                4         5              6            7         8         9
        123456789012345678901234567890  1ab2345   6789012345678/89   012abc345678901234   67890-234567890123abc3456789012334
VH3  1-3   EVQLVESGGGVVRPGGSLRLSCAASGFTFD  D--YGMS   WVRQAPGKGLEWVS    GINW--NGGSYYADSVKG   RFTISRDNAKNSLYLQMNSLRAEDTAVYYCAR} SEQ 29 (VYY)
                                          SEQ 29                      SEQ 30                                                 SEQ 28 (LYH)
```

NOTE: For Hib-1 CDR3: "VYY" replaces the "LYH" that is present at positions 89-91 within VH3 1-3 3-20.

VH CDR3: LKMPHA SEQ 39

JH - Amino acid sequence alignment
```
         CDR3                          H3
              100                   110
               |                      |
JH1     -------WGQGTLVTVSS
```

VL Exon - Amino acid sequence alignment
```
                    FR1                               CDR1              FR2              CDR2                    FR3                                    CDR3
               1         2         3                                 4         5              6          7         8          9
        123456789012345678901234567890    3     456789012abc234      5678901234567     01abcde23456   789012345678ab90123456789012345678   901234Sabcde
VL3 11-7  SSELTQDPAVSVALGQTVRITC            QQ-DS-LRSY-YAS            WYQQKPGQAPVLVIY   GK------NNRPS    GIPDRFSGSSSG--NTASLTITGAQEDEADYC    NSRDSSGNH} SEQ 42
                                            SEQ 43                                      SEQ 44                                              SEQ 45
```

JL - Amino acid sequence alignment
```
         CDR3
              100
               |
JL3     --VFGGGTKLTVL
```

Full Sequence of Hib-1: (Underlined linker sequence is from vector, not actual immunoglobulin chains.)

EVQLVESGGGVVRPGGSLRLSCAASGFTFDDYGMSWVRQAPGKGLEWVSGINWNGGSTYYADSVKGRFTISRDNAKNSLYLQMNSLRAEDTAVYYCARLKMPHAWQGTLVTVSSGGGGSGGGGSGGGGSALSSELTQDPAV
SVALGQTVRITCQQDSLRSYYASWYQQKPGQAPVLVIYGKNNRPSGIPDRFSGSSSGNTASLTITGAQAEDEADYYCNSRDSSGNHVFGGGTKLTVLG

FIG. 5

HIb-3

VH Exon - Amino acid sequence alignment

```
                                    H1                               H2
                                  CDR1                             CDR2                                     CDR3
                FR1                                 FR2                              FR3
         1         2         3              4                  5         6         7         8         9
         1234567890123456789012345678901234567890   1ab2345 6789012345678901abc234   01abcde23456789012345   6789012345678901abc3456789012abcde3456789012345abcde...

HIb-H2  Locus
VH3  1-3  EVQLVESGGGLVQPGGSLRLSCAASGFTFS  S--YAMS  WVRQAPGKGLEWVS  AISG--SGSTYYADSVKG  RFTISRDNSKNTLYLQMNSLRAEDTAVYYCAW }SEQ 35 (V)
                                          SEQ 37                    SEQ 38                                    SEQ 36 (L)

NOTE: For HIb-3 the "V" replaces the "L" at position 5 and the "W" replaces the "R" at position 94 that are present within VH 1-3 3-23.

VH CDR3: KSLLML SEQ 41

JH - Amino acid sequence alignment
         CDR3
              100        110
              |          |
JH1      ---WGQGTLVTVSS
```

VL Exon - Amino acid sequence alignment

```
                                    CDR1                             CDR2                                        CDR3
                FR1                                 FR2                              FR3
         1         2         3              4                  5         6         7         8         9
         123456789012345678901234567890123  45678901abc234   56789012345678901   01abcde23456   789012345678ab9012345678901234567 8901234abcde CDR1-2   Locus                                       SEQ 52                    SEQ 53
VL3  11-7  SSELTQDPAVSVALGQTVRITC  QG-DS-LRSY-YAS  WYQQKPGQAPVLVIY  GK-----NNRPS  GIPDRFSGSSSG--NTASLTITGAQAEDEADYYC  NSRDSSGNH } SEQ 51
                                                                                                              SEQ 54
JL - Amino acid sequence alignment
         CDR3
              100
              |
JL3      -VFGGGTKLTVL
```

Full Sequence of HIb-3: (Underlined linker sequence is from vector, not actual immunoglobulin chains.)

EVQLVESGGGLVQPGGSLRLSCAASGFTFSSYAMSWVRQAPGKGLEWVSAISGSGSTYYADSVKGRFTISRDNSKNTLYLQMNSLRAEDTAVYYCAW KSLLMLWGQGTLVTVSSGGGSGGGSGGGSGGGSALSSELTQDPAV } SEQ 24
SVALGQTVRITCQGDSLRSYYASWYQQKPGQAPVLVIYGKNNRPSGIPDRFSGSSSGNTASLTITGAQAEDEADYYCNSRDSSGNHVFGGGTKLTVLG

*FIG. 7*

HIb-5

VK Exon - Amino acid sequence alignment

```
                       FR1                          CDR1              FR2             CDR2              FR3                          CDR3
                                                    L1                                L2                                             L3
                                                    -----             ----            ----              --------                     ----
                 1         2         3        4567890abcdef234  567890123456789    0123456      7890123456789012345678       9012345ab
        12345678901234567890123                                                                 6         7         8
                                                  SEQ 55                             SEQ 56                                    SEQ 57
L1-L2-L3   Locus
VKII 4-1-(1) A3  DVVMTQSPLSLPVTPGEPASISC  RSSQSLLHS-NGYNYLD   WYLQKPGQSPQLLIY    LGSNRAS      GVPDRFSGSGSGTDFTLKISRVEAEDVGVYYC   MQALQTPPF} SEQ 59 (V)(PF)
                                                                                                                                 SEQ 58(-PF) SEQ 60 (I)(-PF)
```

NOTE: For HIb-5 "V" replaces the "I" that is present at position 2, and an additional "PF" follows position 95 within VKII 4-1(1) A3.

JK - Amino acid sequence alignment

```
         L3
         --
CDR3     |
         100
         |
JK2    -TFGQGTKLEIK
```

Sequenced region of HIb-5: (Underlined linker sequence is from vector, not actual immunoglobulin chains.)

<u>SSGGGGSGGGGSGGGGSAL</u> DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPPFTFGQGTKLEIKR} SEQ 25

*FIG. 8*

HIb-6

There is some homology in the light chain with VK Exon VKII 3-1-(1) O11. However, while the general structure of the VK exon appears appropriate, the number of deviations of specific amino acids from VKII 3-1-(1) O11 are so numerous, that HIb-6 would appear to have a VK unique enough to warrant receiving its own numerical assignment.

VK Exon - Amino acid sequence:   EIVMTQTPLSLSITPGEQASMSCRSSQSLLHSDGYTYLYWFLQKARPVSTLLICEVSNRFSGVPDRFSGSGSGTDFTLKISRVEAEDVGVYYCMQDAQDP } SEQ 61

JK - Amino acid sequence alignment

```
     L3
     -
     CDR3
     --
     100
     |
JK2  -TFGQGTKLEIK
```

Sequenced region of HIb-6: (Underlined linker sequence is from vector, not actual immunoglobulin chains.)

<u>SSGGGGSGGGGSGGGSAL</u>EIVMTQTPLSLSITPGEQASMSCRSSQSLLHSDGYTYLYWFLQKARPVSTLLICEVSNRFSGVPDRFSGSGSGTDFTLKISRVEAEDVGVYYCMQDAQDPTFGQGTKLEIKR } SEQ 26

*FIG. 9*

Hlb-1 Human Anti-GPIbα
DIRECT WESTERN BLOT WITH 9E10 (ANTI-c-myc)

−29 kDa

Sup    Peri

SEQUENCE LISTING

```
<160> NUMBER OF SEQ ID NOS: 62

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:Mimotope
      peptide directed  to human monoclonal antibody
      C-34

<400> SEQUENCE: 1

Ala Trp Asn Trp Arg Tyr Arg Glu Tyr Val
1               5                   10

<210> SEQ ID NO 2
<211> LENGTH: 339
<212> TYPE: DNA
<213> ORGANISM: Homo sapiens

<400> SEQUENCE: 2
gaggtgcagc tggtggagtc tgggggaggt gtggtacggc ctgggggtc cctgagactc      60 tcctgcgcag cctctggatt cacctttgat gattatggca tgagctgggt ccgccaagct     120
ccagggaagg ggctggagtg ggtctccggt attaattgga atggtggtag cacaggttat     180
gcagactctg tgaagggccg attcaccatc tccagagaca acgccaagaa ctccctgtat     240
ctgcaaatga acagcctgag agccgaggac acggccgtgt attactgtgc aagattgaag     300
```

```
atgcctcatg cgtggggcca aggtaccctg gtcaccgtc            339
```

<210> SEQ ID NO 3
<211> LENGTH: 300
<212> TYPE: DNA
<213> ORGANISM: Homo sapiens

<400> SEQUENCE: 3

```
gggtccctta gactctcctg tgcagcctct ggattcactt tcagtaacgc ctggatgagc    60
tgggtccgcc aggctccagg aaggggctg gagtgggttg ccgtattaa agcaaaact     120
gatggtggga caacagacta cgctgcaccc gtgaaaggca gattcaccat ctcaagagat   180
gattcaaaaa acacgctgta tctgcaaatg aacagcctga aaccgagga cacggccgtg    240
tattactgtg caagaaatcc gaagttggtg aagtggggcc aaggtaccct ggtcaccgtc   300
```

<210> SEQ ID NO 4
<211> LENGTH: 336
<212> TYPE: DNA
<213> ORGANISM: Homo sapiens

<400> SEQUENCE: 4

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc atggaagtct   300
ttgcttatgc tttggggcca aggtaccctg gtcacc                             336
```

<210> SEQ ID NO 5
<211> LENGTH: 324
<212> TYPE: DNA
<213> ORGANISM: Homo sapiens

<400> SEQUENCE: 5

```
tcttctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa acaaccggc cctcagggat cccagaccga    180
ttctctggct ccagctcagg aaacacagct tccttgacca tcactgggc tcaggcggaa    240
gatgaggctg actattactg taactcccgg gacagcagtg taaccacgt attcggcgga    300
gggaccaagc tgaccgtcct aggt                                          324
```

<210> SEQ ID NO 6
<211> LENGTH: 330
<212> TYPE: DNA
<213> ORGANISM: Homo sapiens

<400> SEQUENCE: 6

```
cagtctgtgc tgactcagcc accctcagcg tctgggaccc ccgggcagag ggtcaccatc    60
tcttgttctg gaagcagctc caacatcgga agtaattatg tatactggta ccagcagctc   120
ccaggaacgg ccccccaaact cctcatctat aggaataatc agcggccctc agggtccct    180
gaccgattct ctggctccaa gtctggcacc tcagcctccc tggccatcag tgggctccgg   240
tccgaggatg aggctgatta ttactgtgca gcatgggatg acagcctgtt gagtgtattc   300
ggcggaggga ccaagctgac cgtcctaggt                                    330
```

<210> SEQ ID NO 7
<211> LENGTH: 324
<212> TYPE: DNA
<213> ORGANISM: Homo sapiens

<400> SEQUENCE: 7

| | | | | | | |
|---|---|---|---|---|---|---|
| tcttctgagc | tgactcagga | ccctgctgtg | tctgtggcct | tgggacagac | agtcaggatc | 60 |
| acatgccaag | agacagcct | cagaagctat | tatgcaagct | ggtaccagca | gaagccagga | 120 |
| caggcccctg | tacttgtcat | ctatggtaaa | acaaccggc | cctcagggat | cccagaccga | 180 |
| ttctctggct | ccagctcagg | aaacacagct | tccttgacca | tcactgggc | tcaggcggaa | 240 |
| gatgaggctg | actattactg | taactcccgg | gacagcagtg | gtaaccatgt | attcggcgga | 300 |
| gggaccaagc | tgaccgtcct | aggt | | | | 324 |

<210> SEQ ID NO 8
<211> LENGTH: 342
<212> TYPE: DNA
<213> ORGANISM: Homo sapiens

<400> SEQUENCE: 8

| | | | | | | |
|---|---|---|---|---|---|---|
| gatgttgtga | tgactcagtc | tccactctcc | ctgcccgtca | cccctggaga | gccggcctcc | 60 |
| atctcctgca | ggtctagtca | gagcctcctg | catagtaatg | gatacaacta | tttggattgg | 120 |
| tacctgcaga | agccagggca | gtctccacag | ctcctgatct | atttgggttc | taatcgggcc | 180 |
| tccggggtcc | ctgacaggtt | cagtggcagt | ggatcaggca | cagattttac | actgaaaatc | 240 |
| agcagagtgg | aggctgagga | tgttggggtt | tattactgca | tgcaagctct | acaaactcct | 300 |
| cctttttacgt | tcggccaagg | gaccaagctg | gaaatcaaac | gt | | 342 |

<210> SEQ ID NO 9
<211> LENGTH: 336
<212> TYPE: DNA
<213> ORGANISM: Homo sapiens

<400> SEQUENCE: 9

| | | | | | | |
|---|---|---|---|---|---|---|
| gagattgtga | tgacccagac | tccactctcc | ttgtctatca | cccctggaga | gcaggcctcc | 60 |
| atgtcctgca | ggtctagtca | gagcctcctg | catagtgatg | gatacaccta | tttgtattgg | 120 |
| tttctgcaga | aagccaggcc | agtctccacg | ctcctgatct | gtgaagtttc | caaccggttc | 180 |
| tcaggagtgc | cagataggtt | cagtggcagc | gggtcaggga | cagatttcac | actgaaaatc | 240 |
| agccgggtgg | aggctgagga | tgttggagtt | tattactgca | tgcaagatgc | acaagatccc | 300 |
| acgttcggcc | aagggaccaa | gctggaaatc | aaacgt | | | 336 |

<210> SEQ ID NO 10
<211> LENGTH: 113
<212> TYPE: PRT
<213> ORGANISM: Homo sapiens

<400> SEQUENCE: 10

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Leu Lys Met Pro His Ala Trp Gly Gln Gly Thr Leu Val Thr
                100                 105                 110

Val

<210> SEQ ID NO 11
<211> LENGTH: 113
<212> TYPE: PRT
<213> ORGANISM: Homo sapiens

<400> SEQUENCE: 11

Glu Val Gln Leu Val Glu Ser Gly Gly Val Val Arg Pro Gly Gly
 1               5                  10                  15

Ser Leu Arg Leu Ser Cys Ala Ala Ser Gly Phe Thr Phe Asp Asp Tyr
                 20                  25                  30

Gly Met Ser Trp Val Arg Gln Ala Pro Gly Lys Gly Leu Glu Trp Val
             35                  40                  45

Ser Gly Ile Asn Trp Asn Gly Gly Ser Thr Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Leu Lys Met Pro His Ala Trp Gly Gln Gly Thr Leu Val Thr
                100                 105                 110

Val

<210> SEQ ID NO 12
<211> LENGTH: 100
<212> TYPE: PRT
<213> ORGANISM: Homo sapiens

<400> SEQUENCE: 12

Gly Ser Leu Arg Leu Ser Cys Ala Ala Ser Gly Phe Thr Phe Ser Asn
 1               5                  10                  15

Ala Trp Met Ser Trp Val Arg Gln Ala Pro Gly Lys Gly Leu Glu Trp
                 20                  25                  30

Val Gly Arg Ile Lys Ser Lys Thr Asp Gly Gly Thr Thr Asp Tyr Ala
             35                  40                  45

Ala Pro Val Lys Gly Arg Phe Thr Ile Ser Arg Asp Asp Ser Lys Asn
     50                  55                  60

Thr Leu Tyr Leu Gln Met Asn Ser Leu Lys Thr Glu Asp Thr Ala Val
 65                  70                  75                  80

Tyr Tyr Cys Ala Arg Asn Pro Lys Leu Val Lys Trp Gly Gln Gly Thr
                 85                  90                  95

Leu Val Thr Val
                100

<210> SEQ ID NO 13
<211> LENGTH: 100
<212> TYPE: PRT
<213> ORGANISM: Homo sapiens
```

```
<400> SEQUENCE: 13

Gly Ser Leu Arg Leu Ser Cys Ala Ala Ser Gly Phe Thr Phe Ser Asn
 1               5                  10                  15

Ala Trp Met Ser Trp Val Arg Gln Ala Pro Gly Lys Gly Leu Glu Trp
            20                  25                  30

Val Gly Arg Ile Lys Ser Lys Thr Asp Gly Gly Thr Thr Asp Tyr Ala
        35                  40                  45

Ala Pro Val Lys Gly Arg Phe Thr Ile Ser Arg Asp Asp Ser Lys Asn
    50                  55                  60

Thr Leu Tyr Leu Gln Met Asn Ser Leu Lys Thr Glu Asp Thr Ala Val
65                  70                  75                  80

Tyr Tyr Cys Thr Thr Asn Pro Lys Leu Val Lys Trp Gly Gln Gly Thr
                85                  90                  95

Leu Val Thr Val
            100

<210> SEQ ID NO 14
<211> LENGTH: 112
<212> TYPE: PRT
<213> ORGANISM: Homo sapiens

<400> SEQUENCE: 14

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Trp Lys Ser Leu Leu Met Leu Trp Gly Gln Gly Thr Leu Val Thr
            100                 105                 110

<210> SEQ ID NO 15
<211> LENGTH: 112
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ser Leu Leu Met Leu Trp Gly Gln Gly Thr Leu Val Thr
```

<210> SEQ ID NO 16
<211> LENGTH: 108
<212> TYPE: PRT
<213> ORGANISM: Homo sapiens

<400> SEQUENCE: 16

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Phe Gly Gly Gly Thr Lys Leu Thr Val Leu Gly
                100                 105

<210> SEQ ID NO 17
<211> LENGTH: 110
<212> TYPE: PRT
<213> ORGANISM: Homo sapiens

<400> SEQUENCE: 17

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Leu Ser Val Phe Gly Gly Gly Thr Lys Leu Thr Val Leu Gly
                100                 105                 110

<210> SEQ ID NO 18
<211> LENGTH: 108
<212> TYPE: PRT
<213> ORGANISM: Homo sapiens

<400> SEQUENCE: 18

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

-continued

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Phe Gly Gly Gly Thr Lys Leu Thr Val Leu Gly
            100                 105

<210> SEQ ID NO 19
<211> LENGTH: 114
<212> TYPE: PRT
<213> ORGANISM: Homo sapiens

<400> SEQUENCE: 19

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro Phe Thr Phe Gly Gln Gly Thr Lys Leu Glu Ile
            100                 105                 110

Lys Arg

<210> SEQ ID NO 20
<211> LENGTH: 112
<212> TYPE: PRT
<213> ORGANISM: Homo sapiens

<400> SEQUENCE: 20

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Thr Phe Gly Gln Gly Thr Lys Leu Glu Ile Lys Arg
            100                 105                 110

<210> SEQ ID NO 21
<211> LENGTH: 112
<212> TYPE: PRT
<213> ORGANISM: Homo sapiens

<400> SEQUENCE: 21

Glu Ile Val Met Thr Gln Thr Pro Leu Ser Leu Ser Ile Thr Pro Gly
  1               5                  10                  15

```
            1               5              10              15
Glu Gln Ala Ser Met Ser Cys Arg Ser Ser Gln Ser Leu Leu His Ser
                   20                  25                  30

Asp Gly Tyr Thr Tyr Leu Tyr Trp Phe Leu Gln Lys Ala Arg Pro Val
               35                  40                  45

Ser Thr Leu Leu Ile Cys Glu Val Ser Asn Arg Phe Ser Gly Val Pro
               50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asp
                   85                  90                  95

Ala Gln Asp Pro Thr Phe Gly Gln Gly Thr Lys Leu Glu Ile Lys Arg
               100                 105                 110
```

<210> SEQ ID NO 22
<211> LENGTH: 238
<212> TYPE: PRT
<213> ORGANISM: Homo sapiens

<400> SEQUENCE: 22

```
Glu Val Gln Leu Val Glu Ser Gly Gly Gly Val Val Arg Pro Gly Gly
1               5                  10                  15

Ser Leu Arg Leu Ser Cys Ala Ala Ser Gly Phe Thr Phe Asp Asp Tyr
                   20                  25                  30

Gly Met Ser Trp Val Arg Gln Ala Pro Gly Lys Gly Leu Glu Trp Val
               35                  40                  45

Ser Gly Ile Asn Trp Asn Gly Gly Ser Thr Gly Tyr Ala Asp Ser Val
               50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                   85                  90                  95

Ala Arg Leu Lys Met Pro His Ala Trp Gly Gln Gly Thr Leu Val Thr
               100                 105                 110

Val Ser Ser Gly Gly Gly Gly Ser Gly Gly Gly Gly Ser Gly Gly Ser
               115                 120                 125

Ala Leu Ser Ser Glu Leu Thr Gln Asp Pro Ala Val Ser Val Ala Leu
               130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                   165                 170                 175

Ile Tyr Gly Lys Asn Asn Arg Pro Ser Gly Ile Pro Asp Arg Phe Ser
               180                 185                 190

Gly Ser Ser Ser Gly Asn Thr Ala Ser Leu Thr Ile Thr Gly Ala Gln
               195                 200                 205

Ala Glu Asp Glu Ala Asp Tyr Tyr Cys Asn Ser Arg Asp Ser Ser Gly
               210                 215                 220

Asn His Val Phe Gly Gly Gly Thr Lys Leu Thr Val Leu Gly
225                 230                 235
```

<210> SEQ ID NO 23
<211> LENGTH: 242
<212> TYPE: PRT
<213> ORGANISM: Homo sapiens

<400> SEQUENCE: 23

```
Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Asn Ala
             20                  25                  30
Trp Met Ser Trp Val Arg Gln Ala Pro Gly Lys Gly Leu Glu Trp Val
         35                  40                  45
Gly Arg Ile Lys Ser Lys Thr Asp Gly Gly Thr Thr Asp Tyr Ala Ala
     50                  55                  60
Pro Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                 85                  90                  95
Tyr Cys Ala Arg Asn Pro Lys Leu Val Lys Trp Gly Gln Gly Thr Leu
            100                 105                 110
Val Thr Val Ser Ser Gly Gly Gly Ser Gly Gly Gly Gly Ser Gly
        115                 120                 125
Gly Ser Ala Leu Gln Ser Val Leu Thr Gln Pro Pro Ser Ala Ser Gly
    130                 135                 140
Thr Pro Gly Gln Arg Val Thr Ile Ser Cys Ser Gly Ser Ser Ser Asn
145                 150                 155                 160
Ile Gly Ser Asn Tyr Val Tyr Trp Tyr Gln Gln Leu Pro Gly Thr Ala
                165                 170                 175
Pro Lys Leu Leu Ile Tyr Arg Asn Asn Gln Arg Pro Ser Gly Val Pro
            180                 185                 190
Asp Arg Phe Ser Gly Ser Lys Ser Gly Thr Ser Ala Ser Leu Ala Ile
        195                 200                 205
Ser Gly Leu Arg Ser Glu Asp Glu Ala Asp Tyr Tyr Cys Ala Ala Trp
    210                 215                 220
Asp Asp Ser Leu Leu Ser Val Phe Gly Gly Gly Thr Lys Leu Thr Val
225                 230                 235                 240
Leu Gly
```

<210> SEQ ID NO 24
<211> LENGTH: 238
<212> TYPE: PRT
<213> ORGANISM: Homo sapiens

<400> SEQUENCE: 24

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
             20                  25                  30
Ala Met Ser Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Trp Lys Ser Leu Leu Met Leu Trp Gly Gln Gly Thr Leu Val Thr
            100                 105                 110
Val Ser Ser Gly Gly Gly Gly Ser Gly Gly Gly Gly Ser Gly Gly Ser
```

```
                115                 120                 125
Ala Leu Ser Ser Glu Leu Thr Gln Asp Pro Ala Val Ser Val Ala Leu
            130                 135                 140
Gly Gln Thr Val Arg Ile Thr Cys Gln Gly Asp Ser Leu Arg Ser Tyr
145                 150                 155                 160
Tyr Ala Ser Trp Tyr Gln Gln Lys Pro Gly Gln Ala Pro Val Leu Val
                165                 170                 175
Ile Tyr Gly Lys Asn Asn Arg Pro Ser Gly Ile Pro Asp Arg Phe Ser
            180                 185                 190
Gly Ser Ser Ser Gly Asn Thr Ala Ser Leu Thr Ile Thr Gly Ala Gln
        195                 200                 205
Ala Glu Asp Glu Ala Asp Tyr Tyr Cys Asn Ser Arg Asp Ser Ser Gly
    210                 215                 220
Asn His Val Phe Gly Gly Gly Thr Lys Leu Thr Val Leu Gly
225                 230                 235

<210> SEQ ID NO 25
<211> LENGTH: 131
<212> TYPE: PRT
<213> ORGANISM: Homo sapiens

<400> SEQUENCE: 25

Ser Ser Gly Gly Gly Gly Ser Gly Gly Gly Ser Gly Gly Ser Ala
1               5                   10                  15
Leu Asp Val Val Met Thr Gln Ser Pro Leu Ser Leu Pro Val Thr Pro
            20                  25                  30
Gly Glu Pro Ala Ser Ile Ser Cys Arg Ser Ser Gln Ser Leu Leu His
        35                  40                  45
Ser Asn Gly Tyr Asn Tyr Leu Asp Trp Tyr Leu Gln Lys Pro Gly Gln
    50                  55                  60
Ser Pro Gln Leu Leu Ile Tyr Leu Gly Ser Asn Arg Ala Ser Gly Val
65                  70                  75                  80
Pro Asp Arg Phe Ser Gly Ser Gly Ser Gly Thr Asp Phe Thr Leu Lys
                85                  90                  95
Ile Ser Arg Val Glu Ala Glu Asp Val Gly Val Tyr Tyr Cys Met Gln
            100                 105                 110
Ala Leu Gln Thr Pro Pro Phe Thr Phe Gly Gln Gly Thr Lys Leu Glu
        115                 120                 125
Ile Lys Arg
    130

<210> SEQ ID NO 26
<211> LENGTH: 129
<212> TYPE: PRT
<213> ORGANISM: Homo sapiens

<400> SEQUENCE: 26

Ser Ser Gly Gly Gly Gly Ser Gly Gly Gly Gly Ser Gly Gly Ser Ala
1               5                   10                  15
Leu Glu Ile Val Met Thr Gln Thr Pro Leu Ser Leu Ser Ile Thr Pro
            20                  25                  30
Gly Glu Gln Ala Ser Met Ser Cys Arg Ser Ser Gln Ser Leu Leu His
        35                  40                  45
Ser Asp Gly Tyr Thr Tyr Leu Tyr Trp Phe Leu Gln Lys Ala Arg Pro
    50                  55                  60
Val Ser Thr Leu Leu Ile Cys Glu Val Ser Asn Arg Phe Ser Gly Val
```

```
                65                  70                  75                  80
Pro Asp Arg Phe Ser Gly Ser Gly Ser Gly Thr Asp Phe Thr Leu Lys
                    85                  90                  95
Ile Ser Arg Val Glu Ala Glu Asp Val Gly Val Tyr Tyr Cys Met Gln
                100                 105                 110
Asp Ala Gln Asp Pro Thr Phe Gly Gln Gly Thr Lys Leu Glu Ile Lys
            115                 120                 125
Arg

<210> SEQ ID NO 27
<211> LENGTH: 98
<212> TYPE: PRT
<213> ORGANISM: Homo sapiens

<400> SEQUENCE: 27

Glu Val Gln Leu Val Glu Ser Gly Gly Gly Val Val Arg Pro Gly Gly
  1               5                  10                  15
Ser Leu Arg Leu Ser Cys Ala Ala Ser Gly Phe Thr Phe Asp Asp Tyr
                 20                  25                  30
Gly Met Ser Trp Val Arg Gln Ala Pro Gly Lys Gly Leu Glu Trp Val
             35                  40                  45
Ser Gly Ile Asn Trp Asn Gly Gly Ser Thr Gly Tyr Ala Asp Ser Val
         50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 28
<211> LENGTH: 98
<212> TYPE: PRT
<213> ORGANISM: Homo sapiens

<400> SEQUENCE: 28

Glu Val Gln Leu Val Glu Ser Gly Gly Gly Val Val Arg Pro Gly Gly
  1               5                  10                  15
Ser Leu Arg Leu Ser Cys Ala Ala Ser Gly Phe Thr Phe Asp Asp Tyr
                 20                  25                  30
Gly Met Ser Trp Val Arg Gln Ala Pro Gly Lys Gly Leu Glu Trp Val
             35                  40                  45
Ser Gly Ile Asn Trp Asn Gly Gly Ser Thr Gly Tyr Ala Asp Ser Val
         50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr His Cys
                 85                  90                  95
Ala Arg

<210> SEQ ID NO 29
<211> LENGTH: 5
<212> TYPE: PRT
<213> ORGANISM: Homo sapiens

<400> SEQUENCE: 29

Asp Tyr Gly Met Ser
  1               5
```

<210> SEQ ID NO 30
<211> LENGTH: 17
<212> TYPE: PRT
<213> ORGANISM: Homo sapiens

<400> SEQUENCE: 30

Gly Ile Asn Trp Asn Gly Gly Ser Thr Gly Tyr Ala Asp Ser Val Lys
 1               5                  10                  15
Gly

<210> SEQ ID NO 31
<211> LENGTH: 100
<212> TYPE: PRT
<213> ORGANISM: Homo sapiens

<400> SEQUENCE: 31

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg
            100

<210> SEQ ID NO 32
<211> LENGTH: 100
<212> TYPE: PRT
<213> ORGANISM: Homo sapiens

<400> SEQUENCE: 32

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100

<210> SEQ ID NO 33
<211> LENGTH: 5
<212> TYPE: PRT
<213> ORGANISM: Homo sapiens

<400> SEQUENCE: 33

Asn Ala Trp Met Ser
 1               5

<210> SEQ ID NO 34
<211> LENGTH: 19
<212> TYPE: PRT
<213> ORGANISM: Homo sapiens

<400> SEQUENCE: 34

Arg Ile Lys Ser Lys Thr Asp Gly Gly Thr Thr Asp Tyr Ala Ala Pro
 1               5                  10                  15

Val Lys Gly

<210> SEQ ID NO 35
<211> LENGTH: 98
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Trp

<210> SEQ ID NO 36
<211> LENGTH: 98
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 37
<211> LENGTH: 5
<212> TYPE: PRT
<213> ORGANISM: Homo sapiens

-continued

```
<400> SEQUENCE: 37

Ser Tyr Ala Met Ser
1               5

<210> SEQ ID NO 38
<211> LENGTH: 17
<212> TYPE: PRT
<213> ORGANISM: Homo sapiens

<400> SEQUENCE: 38

Ala Ile Ser Gly Ser Gly Gly Ser Thr Tyr Tyr Ala Asp Ser Val Lys
1               5                   10                  15

Gly

<210> SEQ ID NO 39
<211> LENGTH: 6
<212> TYPE: PRT
<213> ORGANISM: Homo sapiens

<400> SEQUENCE: 39

Leu Lys Met Pro His Ala
1               5

<210> SEQ ID NO 40
<211> LENGTH: 6
<212> TYPE: PRT
<213> ORGANISM: Homo sapiens

<400> SEQUENCE: 40

Asn Pro Lys Leu Val Lys
1               5

<210> SEQ ID NO 41
<211> LENGTH: 6
<212> TYPE: PRT
<213> ORGANISM: Homo sapiens

<400> SEQUENCE: 41

Lys Ser Leu Leu Met Leu
1               5

<210> SEQ ID NO 42
<211> LENGTH: 96
<212> TYPE: PRT
<213> ORGANISM: Homo sapiens

<400> SEQUENCE: 42

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 43
```

```
<211> LENGTH: 11
<212> TYPE: PRT
<213> ORGANISM: Homo sapiens

<400> SEQUENCE: 43

Gln Gly Asp Ser Leu Arg Ser Tyr Tyr Ala Ser
 1               5                  10

<210> SEQ ID NO 44
<211> LENGTH: 7
<212> TYPE: PRT
<213> ORGANISM: Homo sapiens

<400> SEQUENCE: 44

Gly Lys Asn Asn Arg Pro Ser
 1               5

<210> SEQ ID NO 45
<211> LENGTH: 9
<212> TYPE: PRT
<213> ORGANISM: Homo sapiens

<400> SEQUENCE: 45

Asn Ser Arg Asp Ser Ser Gly Asn His
 1               5

<210> SEQ ID NO 46
<211> LENGTH: 98
<212> TYPE: PRT
<213> ORGANISM: Homo sapiens

<400> SEQUENCE: 46

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Tyr Val Tyr Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Leu Ser

<210> SEQ ID NO 47
<211> LENGTH: 98
<212> TYPE: PRT
<213> ORGANISM: Homo sapiens

<400> SEQUENCE: 47

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Tyr Val Tyr Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly
```

<210> SEQ ID NO 48
<211> LENGTH: 13
<212> TYPE: PRT
<213> ORGANISM: Homo sapiens

<400> SEQUENCE: 48

```
Ser Gly Ser Ser Ser Asn Ile Gly Ser Asn Tyr Val Tyr
 1               5                  10
```

<210> SEQ ID NO 49
<211> LENGTH: 7
<212> TYPE: PRT
<213> ORGANISM: Homo sapiens

<400> SEQUENCE: 49

```
Arg Asn Asn Gln Arg Pro Ser
 1               5
```

<210> SEQ ID NO 50
<211> LENGTH: 9
<212> TYPE: PRT
<213> ORGANISM: Homo sapiens

<400> SEQUENCE: 50

```
Ala Ala Trp Asp Asp Ser Leu Leu Ser
 1               5
```

<210> SEQ ID NO 51
<211> LENGTH: 96
<212> TYPE: PRT
<213> ORGANISM: Homo sapiens

<400> SEQUENCE: 51

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95
```

<210> SEQ ID NO 52
<211> LENGTH: 11
<212> TYPE: PRT
<213> ORGANISM: Homo sapiens

<400> SEQUENCE: 52

```
Gln Gly Asp Ser Leu Arg Ser Tyr Tyr Ala Ser
 1               5                  10
```

```
<210> SEQ ID NO 53
<211> LENGTH: 7
<212> TYPE: PRT
<213> ORGANISM: Homo sapiens

<400> SEQUENCE: 53

Gly Lys Asn Asn Arg Pro Ser
 1               5

<210> SEQ ID NO 54
<211> LENGTH: 9
<212> TYPE: PRT
<213> ORGANISM: Homo sapiens

<400> SEQUENCE: 54

Asn Ser Arg Asp Ser Ser Gly Asn His
 1               5

<210> SEQ ID NO 55
<211> LENGTH: 16
<212> TYPE: PRT
<213> ORGANISM: Homo sapiens

<400> SEQUENCE: 55

Arg Ser Ser Gln Ser Leu Leu His Ser Asn Gly Tyr Asn Tyr Leu Asp
 1               5                  10                  15

<210> SEQ ID NO 56
<211> LENGTH: 7
<212> TYPE: PRT
<213> ORGANISM: Homo sapiens

<400> SEQUENCE: 56

Leu Gly Ser Asn Arg Ala Ser
 1               5

<210> SEQ ID NO 57
<211> LENGTH: 9
<212> TYPE: PRT
<213> ORGANISM: Homo sapiens

<400> SEQUENCE: 57

Met Gln Ala Leu Gln Thr Pro Pro Phe
 1               5

<210> SEQ ID NO 58
<211> LENGTH: 7
<212> TYPE: PRT
<213> ORGANISM: Homo sapiens

<400> SEQUENCE: 58

Met Gln Ala Leu Gln Thr Pro
 1               5

<210> SEQ ID NO 59
<211> LENGTH: 102
<212> TYPE: PRT
<213> ORGANISM: Homo sapiens

<400> SEQUENCE: 59

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Phe
            100
```

<210> SEQ ID NO 60
<211> LENGTH: 100
<212> TYPE: PRT
<213> ORGANISM: Homo sapiens

<400> SEQUENCE: 60

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100
```

<210> SEQ ID NO 61
<211> LENGTH: 100
<212> TYPE: PRT
<213> ORGANISM: Homo sapiens

<400> SEQUENCE: 61

```
Glu Ile Val Met Thr Gln Thr Pro Leu Ser Leu Ser Ile Thr Pro Gly
1               5                   10                  15

Glu Gln Ala Ser Met Ser Cys Arg Ser Ser Gln Ser Leu Leu His Ser
            20                  25                  30

Asp Gly Tyr Thr Tyr Leu Tyr Trp Phe Leu Gln Lys Ala Arg Pro Val
            35                  40                  45

Ser Thr Leu Leu Ile Cys Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asp
                85                  90                  95

Ala Gln Asp Pro
            100
```

<210> SEQ ID NO 62
<211> LENGTH: 115
<212> TYPE: PRT
<213> ORGANISM: Homo sapiens -continued

```
<400> SEQUENCE: 62

Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asn Pro Lys Leu Val Lys Trp Gly Gln Gly Thr Leu
            100                 105                 110

Val Thr Val
        115
```

VARIABLE HEAVY CHAIN AND VARIABLE LIGHT CHAIN REGIONS OF ANTIBODIES TO HUMAN PLATELET GLYCOPROTEIN IB ALPHA

This application claims priority of U.S. Provisional Patent Application No. 60/106,275, filed Oct. 30, 1998.

FIELD OF THE INVENTION

The subject invention is directed generally to human platelet glycoprotein Ib alpha, and more particularly to variable heavy chain and variable light chain regions of antibodies to human platelet glycoprotein Ib alpha and uses thereof.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

The platelet glycoprotein Ib/IX (GPIb/IX) receptor for von Willebrand factor (vWf) is believed to consist of a 1:1 heterodimeric complex (Du et al. 1987) between GPIb (160 kDa) and GPIX (17 kDa) in a noncovalent association. GPIb in turn consists of a disulfide-linked 140 kDa alpha chain (GPIb alpha) and a 22 kDa beta chain (GPIb beta) (Fitzgerald and Phillips 1989).

The GPIb/IX complex comprises one of the major transmembrane receptor complexes on blood platelets (Roth 1991; Lopez 1994; Clemetson and Clemetson 1995), mediating von Willebrand factor (vWF)-dependent platelet adhesion. In the 1980's, Miller et al. developed a series of monoclonal antibodies (mab) directed against the GP Ib/IX complex receptor for vWf. In particular, monoclonal antibody C-34 was characterized in detail and it was determined that mab C-34 recognized an epitope within the platelet glycoprotein Ib/IX complex (Miller et al. 1990). In this and subsequent work, Miller et al. showed that monoclonal antibodies C-34, AS-2 and AS-7 were potent inhibitors of the ristocetin-induced aggregation of normal platelets that was dependent upon von Willebrand factor. Miller et al. also showed that the epitopes for all three monoclonal antibodies lay within the GPIb/IX complex.

Attempts to define the binding sites for various monoclonal antibodies have led to the development of epitope libraries. Parmley and Smith developed a bacteriophage expression vector that could display foreign epitopes on its surface (Parmley and Smith 1988). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley and Smith 1988; Cwirla et al. 1990; Scott and Smith 1990; Christian et al. 1992; Smith and Scott 1993).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley and Smith 1988; Scott 1992).

Antibody fragments have also been displayed on the surface of filamentous phage that encode the antibody genes (Hoogenboom and Winter 1992; McCafferty et al. 1990; Vaughan et al. 1996; Tomlinson et al. 1992; Nissim et al. 1994; Griffiths et al. 1994). Variable heavy chain ($V_H$) and variable light chain ($V_L$) immunoglobulin libraries have thus been developed in phage, and phage can be selected by panning with antibody. The encoded antibody fragments can then be secreted as soluble fragments from infected bacteria. This display of antibodies on phage and selection with antigen mimics immune selection and can be used to make antibodies without immunization from a single library of phage (see Hoogenboom and Winter 1992).

A human synthetic $V_H$ and $V_L$ ScFv library was made by recloning the heavy and light chain variable regions from the lox library vectors (Griffiths et al. 1994) into the phagemid vector pHEN2 (see FIG. 1). This "Griffin.1" library is a ScFv phagemid library made from synthetic V-gene segments.

A need continues to exist for the elucidation of the sequence of useful epitopes of antibodies that bind to glycoprotein Ib alpha.

SUMMARY OF THE INVENTION

To this end, the subject invention provides a method of selecting a clone that binds to human platelet glycoprotein Ib alpha using a human variable heavy chain and variable light chain immunoglobulin library. The method comprises: incubating a human variable heavy chain and variable light chain immunoglobulin library with cells expressing human platelet glycoprotein Ib, and selecting clones of the library which bind to the cells; and incubating the selected clones of the library with washed human platelets, and selecting resulting clones which bind to the washed human platelets, wherein the resulting clones bind to human platelet glycoprotein Ib alpha.

The subject invention further provides an isolated nucleic acid molecule encoding a variable heavy chain or a variable light chain region of an antibody, wherein the antibody binds to human platelet glycoprotein Ib alpha and inhibits aggregation of platelets.

The isolated nucleic acid molecules of the invention can be inserted into suitable expression vectors and/or host cells. Expression of the nucleic acid molecules encoding a variable heavy chain or a variable light chain region results in production of variable heavy chain or variable light chain regions of an antibody (wherein the antibody binds to human platelet glycoprotein Ib alpha and inhibits aggregation of platelets) in a host cell.

Further provided is an isolated nucleic acid molecule encoding a variable heavy chain region of an antibody, wherein the antibody binds to human platelet glycoprotein Ib alpha and inhibits aggregation of platelets, the nucleic acid molecule encoding a first amino acid sequence having at least 90% amino acid identity to a second amino acid sequence. The second amino acid sequence is selected from the group consisting of SEQ ID NOs:10–15.

Also provided is an isolated nucleic acid molecule encoding a variable light chain region of an antibody, wherein the antibody binds to human platelet glycoprotein Ib alpha and inhibits aggregation of platelets, the nucleic acid molecule encoding a first amino acid sequence having at least 90% amino acid identity to a second amino acid sequence. The second amino acid sequence is selected from the group consisting of SEQ ID NOs:16–21.

The invention also provides an isolated variable heavy chain or a variable light chain region of an antibody, wherein the antibody binds to human platelet glycoprotein Ib alpha and inhibits aggregation of platelets. Further provided is an isolated variable heavy chain region of an antibody, wherein the antibody binds to human platelet glycoprotein Ib alpha and inhibits aggregation of platelets, the variable heavy chain region having a first amino acid sequence having at least 90% amino acid identity to a second amino acid sequence, the second amino acid sequence selected from the group consisting of SEQ ID NOs:10–15. Also provided is an isolated variable light chain region of an antibody, wherein the antibody binds to human platelet glycoprotein Ib alpha and inhibits aggregation of platelets, the variable light chain region having a first amino acid sequence having at least 90% amino acid identity to a second amino acid sequence, the second amino acid sequence selected from the group consisting of SEQ ID NOs:16–21.

Further provided is an antibody comprising the variable heavy chain or variable light chain region of the subject invention, as well as a composition comprising the antibody. The subject invention further provides a method of inhibiting aggregation of platelets by exposing platelets to the composition. Further provided is a method of binding human platelet glycoprotein Ib alpha by exposing human platelet glycoprotein Ib alpha to the antibody.

Also provided is a method of selecting a variable heavy chain or variable light chain region of an antibody, wherein the antibody inhibits aggregation of platelets. The method comprises: selecting a variable heavy chain or variable light chain region according to the subject invention, wherein each of the variable heavy chain or variable light chain regions has an amino acid sequence; altering the amino acid sequence of the selected variable heavy chain or variable light chain region; constructing an antibody having the altered amino acid sequence of the variable heavy chain or variable light chain region; and determining whether the antibody inhibits aggregation of platelets, wherein the altered variable heavy chain or variable light chain region of an antibody that inhibits aggregation of platelets is thereby selected.

BRIEF DESCRIPTION OF THE DRAWINGS

These and other features and advantages of this invention will be evident from the following detailed description of preferred embodiments when read in conjunction with the accompanying drawings in which:

FIG. 5 illustrates the amino acid sequence with alignment for HIb-1;

FIG. 7 illustrates the amino acid sequence with alignment for HIb-3;

FIG. 8 illustrates the amino acid sequence with alignment for HIb-5;

FIG. 9 illustrates the amino acid sequence with alignment for HIb-6;

DETAILED DESCRIPTION OF THE INVENTION

Figure 1:
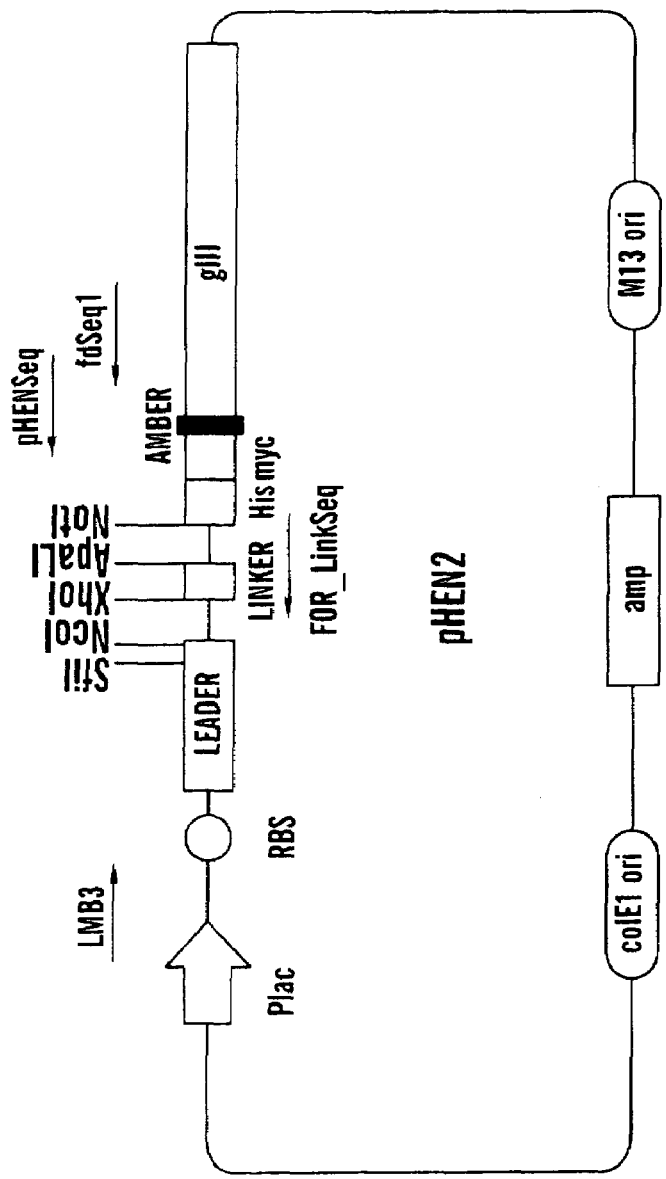
FIG. 1 is a map of the pHEN2 phagemid vector.
Figure 3:
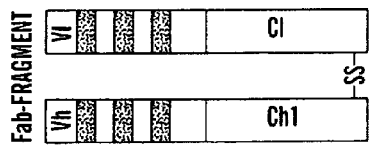
FIG. 3 illustrates the structure of the Fab-fragment of an antibody.
Figure 4:
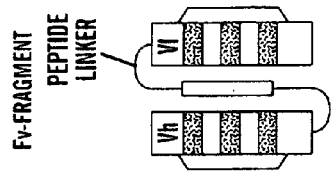
FIG. 4 illustrates the structure of the Fv-fragment of an antibody.
Figure 2:
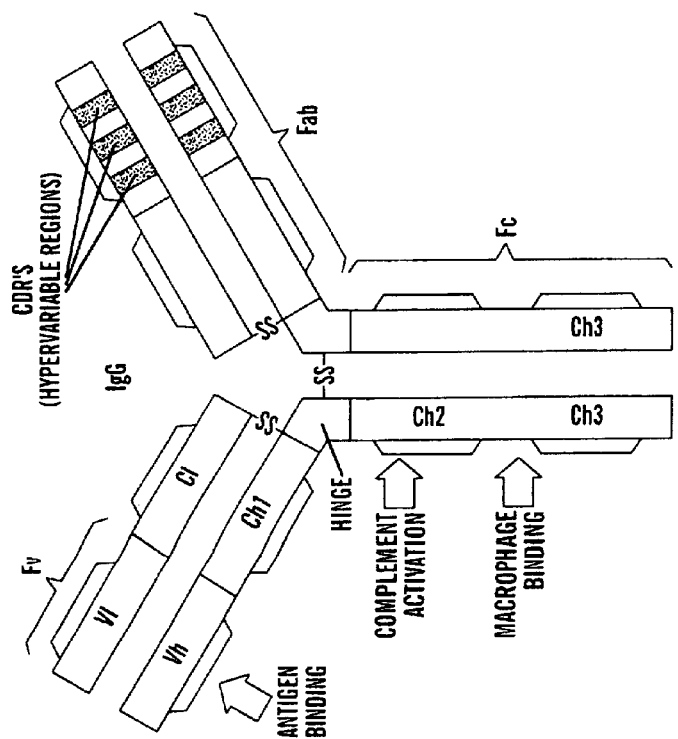
FIG. 2 illustrates the structure of an antibody.
Figure 6:
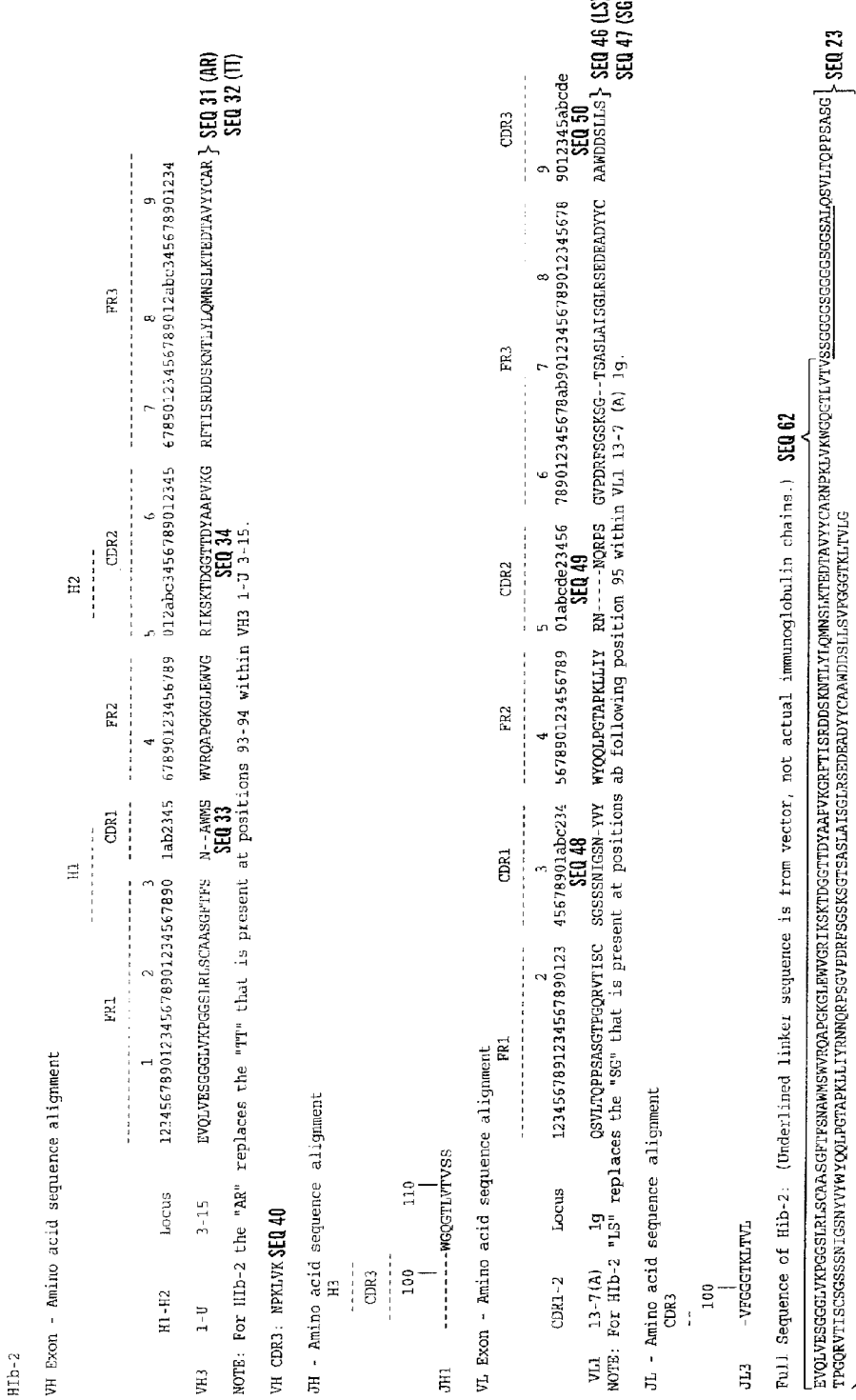
FIG. 6 illustrates the amino acid sequence with alignment for HIb-2.

As used herein, antibody, variable heavy chain ($V_H$ or Vh) and variable light chain ($V_L$ or Vl), Fv fragment, and CDR (hypervariable regions) CDR1, CDR2, CDR3), are used in the context of FIGS. 2–4. FIG. 1 shows a schematic drawing of the organization of a natural IgG and derived recombinant fragments. The Fv fragment is shown as a "Single Chain Fv Fragment" (ScFv) in FIG. 4. In this type of recombinant protein, the two antigen binding regions of the light and heavy chain (Vh and Vl) are connected by a 15–18 amino acid peptide. This linker region permits appropriate interaction between the Vh and Vl regions.

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism in a substantially purified form (i.e. substantially free of other substances originating from that organism), and to synthetic nucleic acid.

By a nucleic acid sequence "homologous to" or "complementary to", it is meant a nucleic acid that selectively hybridizes, duplexes or binds to DNA sequences encoding the variable heavy ($V_H$) or variable light ($V_L$) chain or portions thereof when the DNA sequences encoding the variable heavy ($V_H$) or variable light ($V_L$) chain are present in a human genomic or cDNA library. A DNA sequence which is similar or complementary to a target sequence can include sequences which are shorter or longer than the target sequence so long as they meet the functional test set forth.

Typically, the hybridization is done in a Southern blot protocol using a 0.2× SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6× SSC refers to a solution having a sodium chloride and sodium citrate concentration of 6 times this amount or 0.9 M sodium chloride and 120 mM sodium citrate. 0.2× SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide (in this case, a variable heavy ($V_H$) or variable light ($V_L$) chain). The nucleic acid sequences include both the DNA strand sequence that is transcribed into RNA and the RNA sequence that is translated into protein or peptide (or variable heavy ($V_H$) or variable light ($V_L$) chain). The nucleic acid molecule includes both the full length nucleic acid sequences as well as non-full length sequences derived from the full length variable heavy ($V_H$) or variable light ($V_L$) chain. It being further understood that the sequence includes the degenerate codons of the native sequence or sequences which may be introduced to provide codon preference in a specific host cell.

The term "located upstream" as used herein refers to linkage of a promoter upstream from a nucleic acid (DNA) sequence such that the promoter mediates transcription of the nucleic acid (DNA) sequence.

The term "vector", refers to viral expression systems, autonomous self-replicating circular DNA (plasmids), phagemids, and includes both expression and nonexpression plasmids and phagemids. Where a recombinant microorganism or cell is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or the vector may be incorporated within the host's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stably replicated by the cell during mitosis as an autonomous structure, or the plasmid is incorporated within the host's genome.

The term "phagemid" refers to a vector which combines attributes of a bacteriophage and a plasmid.

The phrase "heterologous protein" or "recombinantly produced heterologous protein" refers to a peptide or protein of interest (in this case the variable heavy ($V_H$) or variable light ($V_L$) chain) produced using cells that do not have an endogenous copy of DNA able to express the peptide or protein of interest. The cells produce the peptide or protein because they have been genetically altered by the introduction of the appropriate nucleic acid sequences. The recombinant peptide or protein will not be found in association with peptides or proteins and other subcellular components normally associated with the cells producing the peptide or protein.

The following terms are used to describe the sequence relationships between two or more nucleic acid molecules or polynucleotides, or between two or more amino acid sequences of peptides or proteins (in this case, the variable heavy ($V_H$) or variable light ($V_L$) chain): "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman (1981), by the homology alignment algorithm of Needleman and Wunsch (1970), by the search for similarity method of Pearson and Lipman (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity. Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to polypeptides, the terms "substantial identity" or "substantial sequence identity" mean that two peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to polypeptides, the terms "substantial homology" or "substantial sequence homology" mean that two peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which, when optimally aligned, have approximately the designated percentage of the same amino acids or conservatively substituted amino acids. For example, "95% amino acid homology" refers to a comparison of the amino acids of two polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "substantially purified" or "isolated" when referring to a protein (or peptide), means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein (or peptide) which is the predominant species present in a preparation is substantially purified. Generally, a substantially purified or isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques. A "substantially purified" or "isolated" protein (or peptide) can be separated from an organism, synthetically or chemically produced, or recombinantly produced.

"Biological sample" or "sample" as used herein refers to any sample obtained from a living organism or from an organism that has died. Examples of biological samples include body fluids and tissue specimens.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. High stringency may be attained, for example, by overnight hybridization at about 68° C. in a 6× SSC solution, washing at room temperature with 6× SSC solution, followed by washing at about 68° C. in a 6× SSC solution then in a 0.6×SSX solution.

Hybridization with moderate stringency may be attained, for example, by: 1) filter pre-hybridizing and hybridizing with a solution of 3× sodium chloride, sodium citrate (SSC), 50% formamide, 0.1M Tris buffer at pH 7.5, 5× Denhardt's solution; 2) pre-hybridization at 37° C. for 4 hours; 3) hybridization at 37° C. with amount of labelled probe equal to 3,000,000 cpm total for 16 hours; 4) wash in 2× SSC and 0.1% SDS solution; 5) wash 4× for 1 minute each at room temperature and 4× at 60° C. for 30 minutes each; and 6) dry and expose to film.

The phrase "selectively hybridizing to" refers to a nucleic acid molecule that hybridizes, duplexes or binds only to a particular target DNA or RNA sequence when the target sequences are present in a preparation of total cellular DNA or RNA. By selectively hybridizing it is meant that a nucleic acid molecule binds to a given target in a manner that is detectable in a different manner from non-target sequence under moderate, or more preferably under high, stringency conditions of hybridization. "Complementary" or "target" nucleic acid sequences refer to those nucleic acid sequences which selectively hybridize to a nucleic acid molecule. Proper annealing conditions depend, for example, upon a nucleic acid molecule's length, base composition, and the number of mismatches and their position on the molecule, and must often be determined empirically. For discussions of nucleic acid molecule (probe) design and annealing conditions, see, for example, Sambrook et al. 1989.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the peptide/protein to which the relevant sequence listing relates.

The DNA molecules of the subject invention also include DNA molecules coding for protein analogs, fragments or derivatives of the protein which differ from naturally-occurring forms (the naturally-occurring protein) in terms of the identity or location of one or more amino acid residues (deletion analogs containing less than all of the residues specified for the protein, substitution analogs wherein one or more residues specified are replaced by other residues, and addition analogs wherein one or more amino acid residues is added to a terminal or medial portion of the protein) and which share the functional property of the naturally-occurring form. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

As used herein, a "peptide" refers to an amino acid sequence of three to one hundred amino acids, and therefore an isolated peptide that comprises an amino acid sequence is not intended to cover amino acid sequences of greater than 125 amino acids. Proteins and peptides can contain any naturally-occurring or non-naturally-occurring amino acids, including the D-form of the amino acids, amino acid derivatives and amino acid mimics, so long as the desired function and activity of the protein or peptide is maintained. The choice of including an (L)- or a (D)-amino acid in the proteins or peptides depends, in part, on the desired characteristics of the protein or peptide. For example, the incorporation of one or more (D)-amino acids can confer increased stability on the protein or peptide and can allow a protein or peptide to remain active in the body for an extended period of time. The incorporation of one or more (D)-amino acids can also increase or decrease the pharmacological activity of the protein or peptide.

The proteins or peptides may also be cyclized, since cyclization may provide the proteins or peptides with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC, 46:257 (1981) and Raucher et al., Tetrahedron. Lett., 21:14061 (1980). An amino acid mimic is, therefor, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual protein or peptide based on the modifications to the backbone or side chain functionalities. For example, these types of alterations to the specifically described amino acid substituents can enhance the protein's or peptide's stability to enzymatic breakdown and increase biological activity. Modifications to the peptide backbone similarly can add stability and enhance activity.

One skilled in the art, using the above sequences or formulae, can easily synthesize the proteins or peptides. Standard procedures for preparing synthetic peptides are well known in the art. Peptides can be synthesized using: the solid phase peptide synthesis (SPPS) method of Merrifield (J. Am. Chem. Soc., 85:2149 (1964)) or modifications of SPPS; or, peptides can be synthesized using standard solution methods well known in the art (see, for example, Bodanzsky, M., Principles of Peptide Synthesis, 2nd revised ed., Springer-Verlag (1988 and 1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985).

With these definitions in mind, the subject invention provides a method of selecting a clone that binds to human platelet glycoprotein Ib alpha using a human variable heavy chain and variable light chain immunoglobulin library. The method comprises: incubating a human variable heavy chain and variable light chain immunoglobulin library with cells expressing human platelet glycoprotein Ib, and selecting clones of the library which bind to the cells; and incubating the selected clones of the library with washed human platelets, and selecting resulting clones which bind to the washed human platelets, wherein the resulting clones bind to human platelet glycoprotein Ib alpha.

Preferably, the cells which express the human platelet glycoprotein Ib alpha are Chinese Hamster Ovary cells.

In one embodiment, the method further comprises incubating the selected resulting clones with further platelets and adding an anti-glycoprotein Ib alpha molecule that may displace clones already bound to the further platelets, and selecting the then-resulting clones that are not bound to the further platelets, the then-resulting clones being capable of binding to human platelet glycoprotein Ib alpha. Preferably, the anti-glycoprotein Ib alpha molecule is a murine monoclonal antibody or peptide (such as the murine monoclonal antibody C-34 or the peptide having the amino acid sequence shown in SEQ ID NO:1).

The subject invention further provides an isolated nucleic acid molecule encoding a variable heavy chain or a variable light chain region of an antibody, wherein the antibody binds to human platelet glycoprotein Ib alpha and inhibits aggregation of platelets. The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the variable heavy ($V_H$) or variable light ($V_L$) chain.

An example of such a variable heavy chain region of an antibody is the variable heavy chain having a nucleotide sequence selected from the group consisting of SEQ ID NO: 2, SEQ ID NO: 3, and SEQ ID NO: 4. An example of such a variable light chain region of an antibody is the variable light chain having a nucleotide sequence selected from the group consisting of SEQ ID NOs:5–9. The amino acid sequence encoded by these nucleotide sequences are shown in SEQ ID NOs:10–15 (heavy chains), and SEQ ID NOs: 16–21 (light chains).

The nucleic acid molecules of the subject invention can be expressed in suitable recombinant host cells using conventional techniques. Any suitable host and/or vector system can be used to express the variable heavy chain or variable light chain region of an antibody, wherein the antibody binds to human platelet glycoprotein Ib alpha and inhibits aggregation of platelets. For in vitro expression, CHO cells or other mammalian cells, or Escherichia coli are preferred.

Techniques for introducing the nucleic acid molecules into the host cells may involve the use of expression vectors which comprise the nucleic acid molecules. These expression vectors (such as phagemids, plasmids, and viruses; viruses including bacteriophage) can then be used to introduce the nucleic acid molecules into suitable host cells. For example, DNA encoding the variable heavy chain or variable light chain region of an antibody can be injected into the nucleus of a host cell or transformed into the host cell using a suitable vector, or mRNA encoding the variable heavy chain or variable light chain region can be injected directly into the host cell, in order to obtain expression of variable heavy chain or variable light chain regions of an antibody in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. One such virus widely used for protein production is an insect virus, baculovirus. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

It should be readily apparent that several of these methods can be used to introduce the nucleic acid molecules into the cells of, or implants of cells within, a subject in vivo (gene therapy applications, including human gene therapy). For example, nucleic acid encoding the variable heavy chain and/or variable light chain, or encoding fragments thereof, or encoding an antibody comprising the variable heavy chain and/or variable light chain or fragments thereof, could be introduced in vivo using a mammalian viral vector such as adenovirus. Such a vector could also include and introduce an inducible promoter controlling expression of the nucleic acid, or other suitable positive or negative response element, so that the subject could simply take a "drug" that would turn on or turn off the expression of the nucleic acid of the subject invention. The "drug", for example, could induce the inducible promoter.

Host cells into which the nucleic acid encoding the variable heavy chain or variable light chain region has been introduced can be used to produce (i.e. to functionally express) the variable heavy chain or variable light chain region. The function of the encoded variable heavy chain or a variable light chain region can be assayed according to methods known in the art by incorporating the variable heavy chain or variable light chain region into an antibody, and testing the antibody for its ability to bind to human platelet glycoprotein Ib alpha and to inhibit aggregation of platelets.

The nucleic acid molecules of the subject invention can be used either as probes or for the design of primers to obtain DNA encoding other variable heavy chain or variable light chain regions of an antibody, wherein the antibody binds to human platelet glycoprotein Ib alpha and inhibits aggregation of platelet, by either cloning and colony/plaque hybridization or amplification using the polymerase chain reaction (PCR).

Specific probes derived from the sequences herein can be employed to identify colonies or plaques containing cloned DNA encoding a variable heavy chain or variable light chain region of an antibody using known methods (see Sambrook et al. 1989). One skilled in the art will recognize that by employing such probes under high stringency conditions (for example, hybridization at 42° C. with 5× SSPC and 50% formamide, washing at 50–65° C. with 0.5× SSPC), sequences having regions which are greater than 90% homologous or identical to the probe can be obtained. Sequences with lower percent homology or identity to the probe, which also encode variable heavy chain or variable light chain regions of an antibody, can be obtained by lowering the stringency of hybridization and washing (e.g., by reducing the hybridization and wash temperatures or reducing the amount of formamide employed).

Specific primers derived from the sequences herein can be used in PCR to amplify a DNA sequence encoding a variable heavy chain or variable light chain region of an antibody, wherein the antibody binds to human platelet glycoprotein Ib alpha and inhibits aggregation of platelets, using known methods (see Innis et al. 1990). One skilled in the art will recognize that by employing such primers under high stringency conditions (for example, annealing at 50–60° C., depending on the length and specific nucleotide content of the primers employed), sequences having regions greater than 75% homologous or identical to the primers will be amplified.

Various modifications of the nucleic acid and amino acid sequences disclosed herein are covered by the subject invention. These varied sequences still encode a functional variable heavy chain or variable light chain region of an antibody, wherein the antibody binds to human platelet glycoprotein Ib alpha and inhibits aggregation of platelets. The invention thus further provides an isolated nucleic acid molecule encoding a variable heavy chain region of an antibody, wherein the antibody binds to human platelet glycoprotein Ib alpha and inhibits aggregation of platelets, the nucleic acid molecule encoding a first amino acid sequence having at least 90% amino acid identity to a second amino acid sequence, the second amino acid sequence selected from the group consisting of SEQ ID NOs:10–15. The invention further provides an isolated nucleic acid molecule encoding a variable light chain region of an antibody, wherein the antibody binds to human platelet glycoprotein Ib alpha and inhibits aggregation of platelets, the nucleic acid molecule encoding a first amino acid sequence having at least 90% amino acid identity to a second amino acid sequence, the second amino acid sequence selected from the group consisting of SEQ ID NOs:16–21. In further embodiments, the first amino acid sequence has at least 95%, 96%, 97%, 98%, or 99% amino acid identity to the recited sequence.

Invention further provides an isolated variable heavy chain or a variable light chain region of an antibody, wherein the antibody binds to human platelet glycoprotein Ib alpha and inhibits aggregation of platelets. The variable heavy chain is preferably encoded by a nucleotide sequence selected from the group consisting of SEQ ID NO: 2, SEQ ID NO: 3, and SEQ ID NO: 4. The variable heavy chain preferably has an amino acid sequence selected from the group consisting of SEQ ID NOs:10–15. The variable light chain is preferably encoded by a nucleotide sequence selected from the group consisting of SEQ ID NOs:5–9. The variable light chain preferably has an amino acid sequence selected from the group consisting of SEQ ID NOs:16–21. Further provided is an isolated variable heavy chain region of an antibody, wherein the antibody binds to human platelet glycoprotein Ib alpha and inhibits aggregation of platelets, the variable heavy chain being encoded by a first amino acid sequence having at least 90% amino acid identity to a second amino acid sequence, the second amino acid sequence selected from the group consisting of SEQ ID NOs:10–15. Also provided is an isolated variable light chain region of an antibody, wherein the antibody binds to human platelet glycoprotein Ib alpha and inhibits aggregation of platelets, the variable light chain being encoded by a first amino acid sequence having at least 90% amino acid identity to a second amino acid sequence, the second amino acid sequence selected from the group consisting of SEQ ID NOs:16–21. In further embodiments, the first amino acid sequence has at least 95%, 96%, 97%, 98%, or 99% amino acid identity to the recited sequences.

It should be readily apparent to those skilled in the art that a met residue may need to be added to the amino terminal of the amino acid sequence of the variable heavy chain or variable light chain region or an ATG added to the 5' end of the nucleotide sequence, in order to express the variable heavy chain or variable light chain region in a host cell. The met version of the variable heavy chain or variable light chain region is thus specifically intended to be covered by reference to particular SEQ ID NOs.

The invention further provides an antibody comprising the variable heavy chain or variable light chain region disclosed herein. Antibodies of the subject invention include monovalent, bivalent, and polyvalent antibodies, as well as fragments of these antibodies. Fragments of the antibodies of the present invention include, but are not limited to, the Fab and the F(ab')$_2$ fragments.

The antibodies of the subject invention may be provided in a detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Epitope tags can also be used, such as the c-myc peptide (to which antibodies are available that recognize the small peptide or protein of interest). The 6x-histidine tag (for which there are not only antibodies available but also chelating materials that have a high affinity for the histidines) is also commonly used to purify secreted proteins. Procedures for accomplishing such labeling are well known in the art, for example see Sternberger et al. 1970, Bayer et al. 1979, Engval et al. 1972, and Goding 1976.

Further provided is a composition comprising the antibody and a carrier. The composition can be used to inhibit aggregation of platelets by exposing platelets to the composition. The antibody can also be used to bind to human platelet glycoprotein Ib alpha, the method comprising exposing human platelet glycoprotein Ib alpha to the antibody.

In the methods of the invention, tissues or cells or platelet glycoprotein Ib alpha (a cell surface protein) are contacted with or exposed to the composition or antibody of the subject invention. In the context of this invention, to "contact" tissues or cells or platelet glycoprotein Ib alpha with or to "expose" tissues or cells or platelet glycoprotein Ib alpha to a composition or antibody means to add the composition or antibody, usually in a liquid carrier, to a cell suspension or tissue sample, either in vitro or ex vivo, or to administer the composition or antibody to cells or tissues within an animal (including humans).

The formulation of therapeutic compositions and their subsequent administration is within the skill in the art. In general, for therapeutics, a patient suspected of needing such therapy is given a composition in accordance with the invention, commonly in a pharmaceutically acceptable carrier, in amounts and for periods which will vary depending upon the nature of the particular disease, its severity and the patient's overall condition. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate uptake. One such composition shown to facilitate uptake is LIPOFECTIN (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body and from assessment of the function of platelets obtained from blood specimens from the patient. Persons of ordinary skill can easily determine optimum dosages, dosing methodologies and repetition rates. Optimum dosages may vary depending on the relative potency of individual compositions, and can generally be calculated based on $IC_{50}$'s or $EC_{50}$'s in in vitro and in vivo animal studies. For example, given the molecular weight of compound (derived from oligonucleotide sequence and/or chemical structure) and an effective dose such as an $IC_{50}$, for example (derived experimentally), a dose in mg/kg is routinely calculated.

Once a variable heavy chain or variable light chain of interest is identified, the antibody constructed using the variable heavy chain or variable light chain be used to identify peptides capable of mimicking the inhibitory activity of the antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., Gene 73:305–318 (1988)). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley, S. F. & Smith, G. P., Gene 73:305–318 (1988); Cwirla, S. E., et al., Proc Natl Acad Sci USA 87:6378–6382 (1990); Scott, J. K. & Smith, G. P., Science 249:386–390 (1990); Christian, R. B., et al., J Mol Biol 227:711–718 (1992); Smith, G. P. & Scott, J. K., Methods in Enzymology 217:228–257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., Gene 73:305–318 (1988); Scott, J. K., Trends in Biochem Sci 17:241–245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e. binding sites) offers great potential application.

Using this technique, mimotopes to an antibody that recognizes platelet glycoprotein Ib alpha can be identified. The sequences of these mimotopes represent short peptides which can then be used in various ways, for example as peptide drugs that bind to platelet glycoprotein Ib alpha and inhibit aggregation of platelets. Once the sequence of the mimotope is determined, the peptide drugs can be chemically synthesized.

The antibodies of the subject invention (or fragments thereof) can thus be used to select peptides, mimotopes, etc. that are complementary to the antibodies and that can then be used as antidotes to the antibodies themselves. For example, if a subject being treated with the antibody in order to inhibit platelet aggregation was involved in a motor vehicle accident and the risk of bleeding far exceeded the risk of thrombosis, it would be desirable to turn "off" the antibody of the subject invention. This could be done by using the peptide or mimotope to the antibody itself. The peptide or mimotope could thus be administered to the subject to displace the antibody from the platelets, preventing the antibody-induced inhibition of platelets.

The identified variable heavy chain and variable light chain regions of an antibody, wherein the antibody inhibits aggregation of platelets, can also be used to select additional variable heavy chain and variable light chain regions of an antibody which inhibits aggregation of platelets. Such a method involves the selection of a variable heavy chain or variable light chain region as defined above (for example, SEQ ID NOs:10–15 for heavy chains, SEQ ID NOs:16–21 for light chains), wherein each of the variable heavy chain or variable light chain regions has an amino acid sequence; altering the amino acid sequence of the selected variable heavy chain or variable light chain region; constructing an antibody having the altered amino acid sequence of the variable heavy chain or variable light chain region; and determining whether the antibody inhibits aggregation of platelets, wherein the altered variable heavy chain or variable light chain region of an antibody that inhibits aggregation of platelets is thereby selected.

EXAMPLE I

Full DNA sequences were isolated from the Human Synthetic VH and VL ScFv Library (the Griffin.1 Library, available from the Medical Research Council in England), and the protein sequences of multiple ScFv clones were determined. The ScFv clones were selected on the basis of their binding to platelet GPIb. Whether displayed as surface proteins on the phagemid or secreted as free ScFv by *E. coli*, several of these different ScFv clones have proven capable of inhibiting von Willebrand factor (vWF)-dependent aggregation of platelets, most likely due to their altering the binding site for vWF that is known to be contained within GPIb. Since the Griffin.1 Library was constructed from native human antibody heavy and light chain variable sequences, ScFv isolated from this library are comprised of native human protein sequences—and hence very attractive potential reagents for therapeutic purposes. The ScFv provide a new class of anti-thrombotic agents, useful for the prevention of platelet-dependent thrombi in diseased arteries, bypass grafts, dialysis access, etc. In contrast to antibodies derived from mouse or other species, the human ScFv stand a far better chance of being recognized as self, rather than as a foreign protein.

In addition to the potential anti-thrombotic uses of the isolated ScFv, these ScFv are also useful as diagnostic reagents in human medicine. Since GPIb is a highly restricted antigen in its expression throughout the body, it has turned out to be one of the best markers to identify platelets, their precursor cell (the megakaryocyte), and leukemic blast cells of megakaryocytic origin. Additionally, there is some evidence in the literature that assaying a soluble form of platelet GPIb in the plasma (that presumably results from proteolytic degradation of platelet surface GPIb) may be useful as a clinical marker. The new anti-GPIb ScFv are readily harvested from *E. coli* cultures, rather than from the mammalian cells required for murine monoclonal antibodies, and may therefore be a more economical source of anti-GPIb markers for diagnostic uses than were previously available.

Since the human ScFv are directed against platelet glycoprotein Ib, they have been named HIb-1, HIb-2, HIb-3, etc., so as to reinforce the source of the ScFv (Human) and the target of the ScFv (Ib). In the case of HIb-1, HIb-2, and HIb-3, DNA sequencing has provided the amino acid sequences of both the heavy chain and light chain variable regions contributing to the ScFv, including VH exon, particular VH CDR3, JH, linker sequence, VL exon, particular VL CDR3, and JL segments. In the case of HIb-5 and HIb-6, DNA sequencing has thus far provided the amino acid sequences of the light chain variable regions contributing to the ScFv.

This technology provides advantages over existing technology, including:

1. For therapeutic purposes, an anti-platelet antibody of human sequence may obviate the human anti-mouse antibody reaction seen when murine antibodies are used. Platelet GPIb is an important target for anti-thrombotics that is only now beginning to be appreciated.

2. The ScFv are produced by bacterial cultures, which potentially may be more economical than the mammalian cell cultures required for murine antibodies.

3. Since the ScFv are fully cloned, the opportunity to make modifications of the basic ScFv molecules is readily available.

4. Since these ScFv were selected without immunization of animals, it is possible that one or more of these ScFv is directed against an epitope within GPIb for which animals might fail to mount an immune response, due to a high degree of structural conservation across species lines. The Griffin.1 library was constructed in such a manner that ScFv directed against normal human antigens are also included in the repertoire.

The ScFv clones were obtained by screening the Griffin.1 Library. The key points in this screening process were that the first steps in the screening procedure utilized CHO cells expressing recombinant GPIb alpha, and then applicant took the subset of the library surviving three rounds of selection against these cells, and then applicant went into a 4th round against normal washed human platelets. Applicant then did two final rounds where applicant attempted to displace ScFv from washed platelets by flooding them with a lot of murine monoclonal antibody (C-34 or SZ-2) or mimotope peptide (AWNWRYREYV).

The human synthetic $V_H$ and $V_L$ ScFv library was made by recloning the heavy and light chain variable regions from the lox library vectors (Griffiths et al. 1994) into the phagemid vector pHEN2 (see FIG. 1). This "Griffin.1" library is a ScFv phagemid library made from synthetic V-gene segments. The kappa and lambda light chain variable regions were PCR amplified from fdDOG-2loxVk and VL constructs. The PCR fragments were purified and digested with ApaL1 and Not 1. The gel purified fragments were then ligated into the vector pHEN2. Heavy chain variable regions were PCR amplified from the pUC19-2loxVH vector. The PCR fragments were purified and digested with Sfi1 and Xho1. The gel purified fragments were then ligated into the vector Vk-pHEN2 or VL-pHEN2.

The isolation of the HIb series of ScFv was performed as follows:

Initial three rounds of phagemid selection against transfected Chinese Hamster Ovary (CHO) cells expressing only the GPIb alpha component of the GPIb/IX/V complex on their surface $10^{12}$–$10^{13}$ phagemid incubated 1.5 hours at RT with transfected CHO cells adherent to culture flask Unbound phagemid removed by extensive washing Bound phagemid eluted with triethylamine, neutralized with Tris, infected into E. coli suppressor strain TG1, and amplified (using helper phage) for use in next round Monoclonal phagemid clone HIb-3 is a representative clone from this stage of selection Round 4 of selection: Against washed human platelets $10^{12}$ phagemid incubated with a suspension of washed platelets for 1.5 hours at RT Unbound phagemid removed by extensive washing of platelets Bound phagemid eluted with triethylamine, neutralized with Tris, infected into E. coli, and amplified for use in next round Monoclonal phagemid clone HIb-3 is a representative clone from this stage of selection Rounds 5 and 6 of selection: Displacement of phage bound to platelets (optional)

Round 5: $10^{12}$ Phage from round four incubated with $3 \times 10^9$ washed platelets, unbound phage removed by extensive washing, and platelets then divided into three aliquots Incubation of platelets for 90 min at RT with 25 µg/mL anti-GPIb alpha murine mabs C-34 or SZ-2 or 200 µg/mL C-34 mimotope peptide AWNWRYREYV Phagemid recovered from buffer then infected into E. coli, and amplified for use in next round Round 6: amplified phage from fifth round bound to washed platelets and then challenged with same potential displacer as used in round 5

Production of ScFv from Round 6 Phagemids

Phagemid recovered from round 6 infected into E. coli non-suppressor strain HB2151

24-well monoclonal culture supernatants assayed in Western blots against platelet lysates and for ability to inhibit ristocetin-induced aggregation of washed human platelets Interesting clones scaled up for DNA sequencing and further functional studies on purified ScFv This work employs ScFv technology in the development of a new family of antibody molecules directed against human platelet GPIbα—molecules that are themselves derived from human immunoglobulin variable sequences. As an alternative to natural IgG antibodies, synthetic monovalent antibodies with increasingly high affinities can be made from the heavy chain variable and light chain variable regions, separated by a linker region. Such synthetic variable antibodies are termed ScFv. The Griffin.1 synthetic ScFv library, composed of human germline VH and VL sequences used for these studies was produced by the laboratory of Dr. Greg Winter of the MRC in Cambridge, UK. As posted on this laboratory group's web page, "This library contains exactly the same synthetic human V-genes as the Human Synthetic Fab (4–12) 2lox Library (Griffiths, A. D. et. al., (1994). EMBO J. 13, 3245–3260) but is in a single chain Fv (scFv) format instead of an Fab format. The vector is also a phagemid rather than a phage so it is like the Human Synthetic scFv Library or "Nissim Library" (Nissim, A. et al., (1994). EMBO J. 13, 692–698) but with diversity in the light chains as well as the heavy chains." In addition to the in vitro recombination of heavy and light chains, this library has achieved an estimated total diversity of $1.2 \times 10^9$ clones through in vitro randomization at the hypervariable CDR3 regions. The resulting VH and VL coding sequences were then cloned into the pHEN2 phagemid. Depending upon whether the phagemid is infected into a strain of E. coli lacking or possessing a suppressor for the amber codon, one can then obtain either progeny phagemid expressing the ScFv in fusion with a major phage coat protein, or a secreted form of the ScFv. The secreted ScFv also contain a 6x-His tag which can be used in protein purification and a c-myc tag for detection with an anti-c-myc antibody such as 9E10.

For the present studies, the initial round of phagemid selection was performed against transfected Chinese Hamster Ovary (CHO) cells expressing only the GPIbα component of the GPIb/IX/V complex on their surface. $10^{12}$–$10^{13}$ phagemid were incubated for 1.5 hours at RT with transfected CHO cells adherent to the culture flask. Unbound phagemid were removed by extensive washing, and bound phagemid were eluted with triethylamine, neutralized with Tris, infected into the E. coli suppressor strain TG1, and then amplified (using helper phage) for use in the next round. This process was then repeated for two additional rounds.

For the $4^{th}$ round of selection, we performed a "crossover" step, using human platelets. We aimed by this approach to significantly enrich for phagemid recognizing epitopes present only on both the CHO cell and the platelet, thereby increasing the odds of finding ScFv with specificities for GPIbα. Monoclonal phagemid clone HIb-3 is a representative clone from this stage of selection. Whereas the polyclonal collection of all $4^{th}$ round phagemid did identify GPIbα in Western blots, most individual clones tested did not. Moreover, random conversion of Round 4 phagemid clones to soluble ScFv did not yield ScFv that exhibited inhibitory activity in functional assays.

We accordingly proceeded to additional rounds, designed so as to try to direct the selection of epitopes most relevant to the vWF binding function of GPIbα. Towards this end, phage from round 4 were incubated with washed platelets, and unbound phage removed by extensive washing. Platelets were then further incubated with saturating concentrations of the anti-GPIbα murine mabs C-34 or SZ-2 or with C-34 mimotope peptide, which we have previously shown to compete with platelets for binding to C-34. Phage recovered in the buffer following these incubations were amplified, and then used in a $6^{th}$ and final round, in which displacement of phage was again attempted with the same mab or peptide used with it in the previous round.

Phagemid recovered from round 6 were directly infected into the E. coli non-suppressor strain HB2151. Secreted ScFv from overnight supernatants were assayed in Western blots against platelet lysates and were tested for their ability to inhibit ristocetin-induced aggregation of washed human platelets. Interesting clones were then chosen for further study.

A particularly prominent clone (HIb-1) was observed whether SZ-2, C-34, or C-34 mimotope peptide was used as displacer. Clone HIb-2 was uniquely seen when SZ-2 was used as displacer. Clone HIb-3, as stated above, was derived from an earlier round of selection. Clones HIb-5 and HIb-6 were recovered in the buffer when C-34 mimotope peptide was used as displacer.

Figure 10:
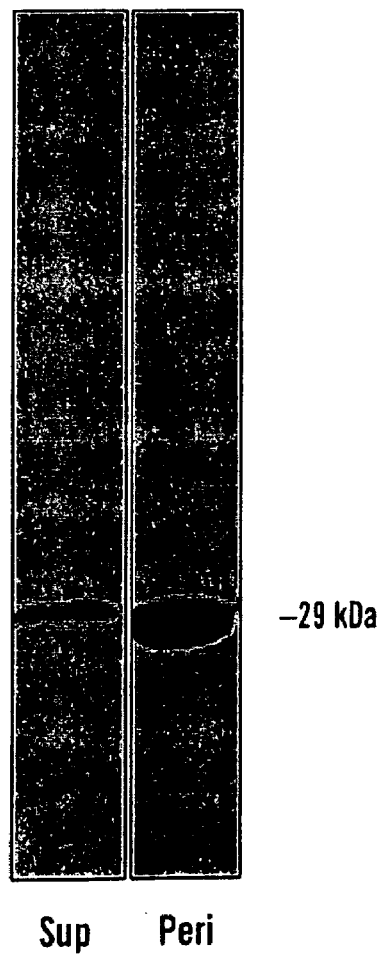
FIG. 10 is a direct western blot of HIb-1 human anti-GPIb alpha.

The purified HIb ScFv, whether purified from culture supernatants or from periplasmic spaces, had the anticipated molecular weight of 29 kilodaltons. This is illustrated in FIG. 10, where both crude supernatant and purified periplasmic fraction from an E. coli culture were run on SDS-polyacrylamide gel electrophoresis (SDS-PAGE), electroblotted, and then incubated with the murine monoclonal antibody 9E10, which recognizes the c-myc epitope tag contained within the secreted ScFv. Peroxidase-conjugated secondary anti-mouse antibody was then used to detect the presence of bound 9E10.

Figure 11:
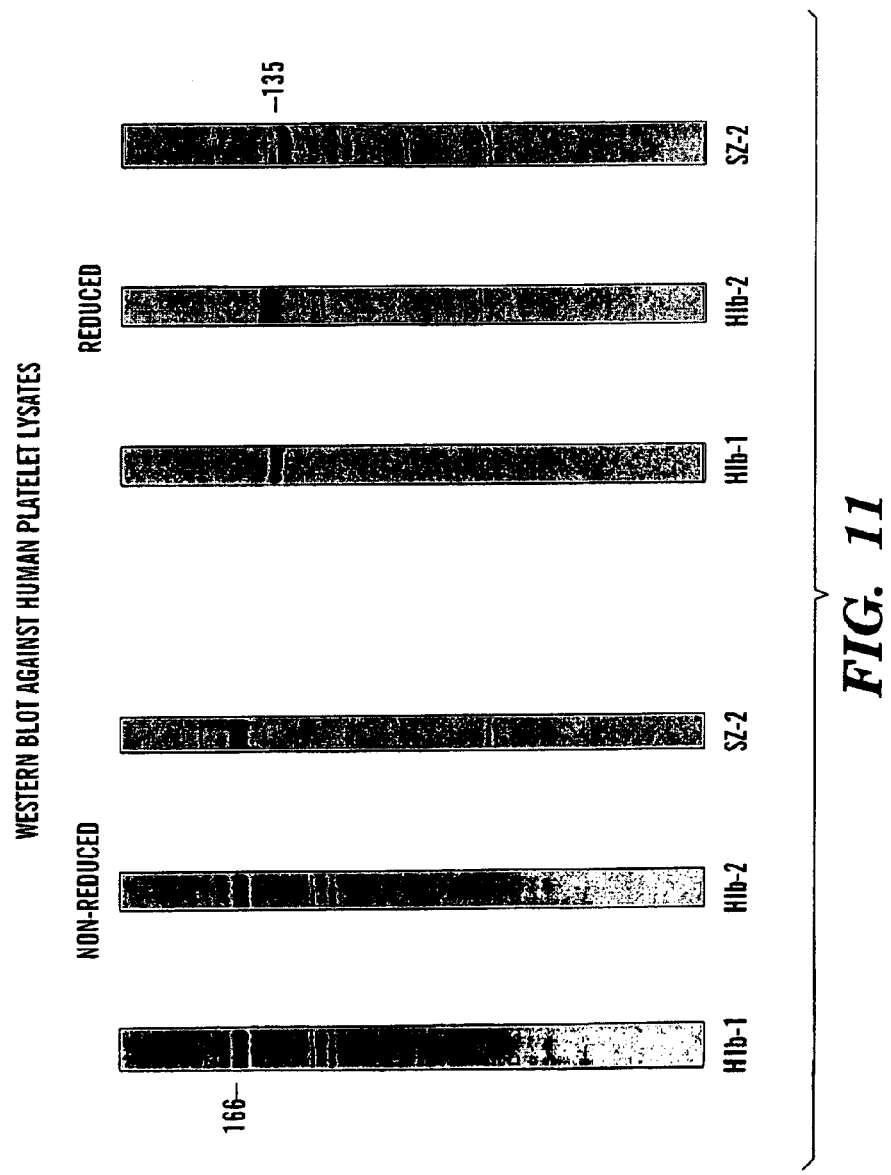
FIG. 11 shows western blots of HIb-1, HIb-2 and SZ-2 under non-reduced and reduced conditions.

The binding specificity of selected clones with respect to epitope targets deriving from human platelets was also established by immunoblotting. Detergent lysates of platelets obtained from human blood were prepared, and were electrophoresed by SDS-PAGE either under non-reducing conditions or following reduction with b-mercaptoethanol. GPIbα has an apparent molecular mass of 135–140 kDa when electrophoresed under reducing conditions in this system, but characteristically migrates with an apparent molecular mass in the 160–170 kDa region under non-reducing conditions, reflecting the additional mass of GPIbB with which it is covalently bonded in the non-reduced, native state. Following electroblotting to a membrane, the electrophoresed platelet lysates were then probed with either the well-established anti-GPIbα murine monoclonal antibody SZ-2, or with a product from one of the selected clones. Detection of binding of the SZ-2 employed a peroxidase-labeled secondary anti-mouse antibody, as described above. In the earlier rounds of selection, phagemid from selected clones were directly incubated with the blots, and following washings, the residual binding of phagemid was detected through the use of an anti-M13 bacteriophage antibody, since the M13 surface epitope for this antibody is preserved in the pHEN2 phagemid. This approach permitted ready distinction between clones of phagemid that mimicked the binding pattern seen with SZ-2 from those that did not. Following the later rounds of selection, however, when secreted clonal ScFv became available, the ScFv were used instead of actual phagemid in the immunoblotting. Thus, ScFv secreted by clones HIb-1, HIb-2, HIb-5, and HIb-6, when used as the primary antibody in a Western blot against human platelet lysates, all showed a pattern closely mimicking that of murine monoclonal antibody SZ-2. An example of this is shown in FIG. 11, for HIb-1 and HIb-2 ScFv. Following the initial incubation with and subsequent washings of the membranes with the indicated ScFv, secondary antibody 9E10, and in turn peroxidase-conjugated anti-mouse antibody were incubated with the membrane, and staining developed with peroxidase substrate. As can be seen in this example, the products of the selected clones were able to recognize bands having the migration characteristics of GPIbα, both under non-reducing and reducing conditions.

The ability of products from the selected clones to inhibit platelet function was tested by platelet aggregation. Since a major function of GPIbα is its role as receptor for the adhesive ligand, von Willebrand factor (vWF), vWF-dependent platelet aggregation was of particular interest. In vitro, aggregation involving the binding of vWF to platelet GPIb is conventionally assessed using either ristocetin or botrocetin as mediators. ScFv obtained from clones HIbB-1, HIbB-2, HIbB-5, and HIbB-6 were found to inhibit vWF-dependent platelet aggregation induced by at least one of these mediators. In the case of HIB-3, the phagemid itself showed inhibitory activity in an aggregation assay.

Figure 12:
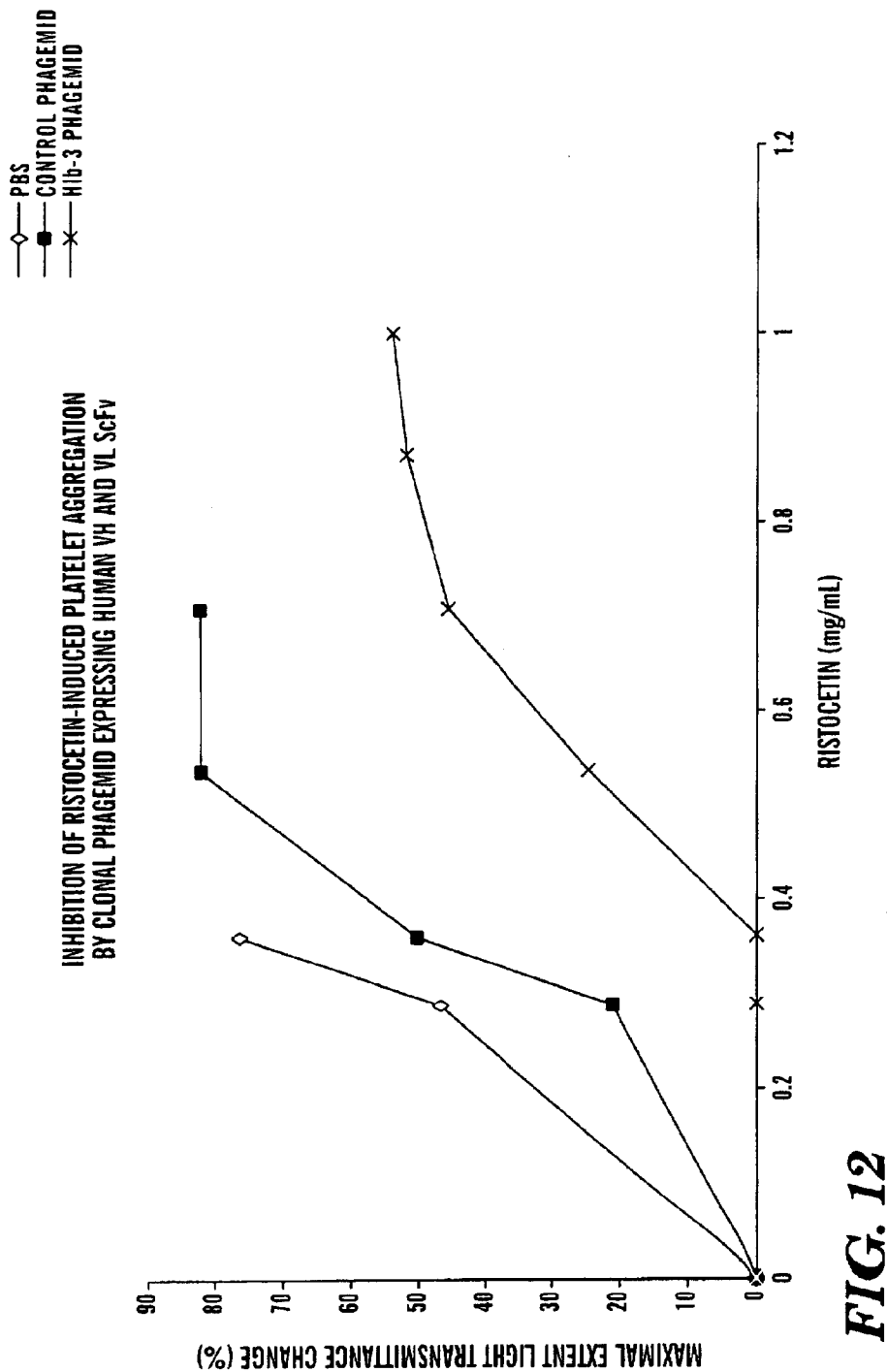
FIG. 12 illustrates inhibition of ristocetin-induced platelet aggregation by clonal phagemid expressing human VH and VL ScFv.

A representative example of inhibition at the phagemid level is shown in FIG. 12. Human platelets that have been formalin-fixed were suspended in buffer containing 5 µg/mL purified vWF at a final platelet concentration of 150,000/µL, added to a cuvette with a stir bar, and stirred at 1200 rpm, 37° C., in a Chronolog Aggregometer. Ristocetin was then added at varying final concentrations, and resulting change in light transmittance used as an indicator of platelet aggregation. As can be seen in the figure, pre-incubation for 1.5 hour of the platelets (at 150,000/µL) with $1\times10^{12}$ HIbB-3 phagemid totally inhibited platelet aggregation at ristocetin concentrations at or below 0.35 mg/mL in this system, and even at a ristocetin concentration as high as 1.0 mg/mL continued to exert strong inhibition. In contrast, in the presence of an equal concentration of phagemid not expressing activity against platelet GPIbα (Control Phagemid), a full aggregatory response was reached by 0.5 mg/mL ristocetin, with moderate aggregation responses observed in the range of 0.3–0.35 mg/mL ristocetin. (Note that the formalin-fixed platelets characteristically are aggregated in the presence of lower concentrations of ristocetin than is usually required with non-fixed platelets.)

Figure 13:
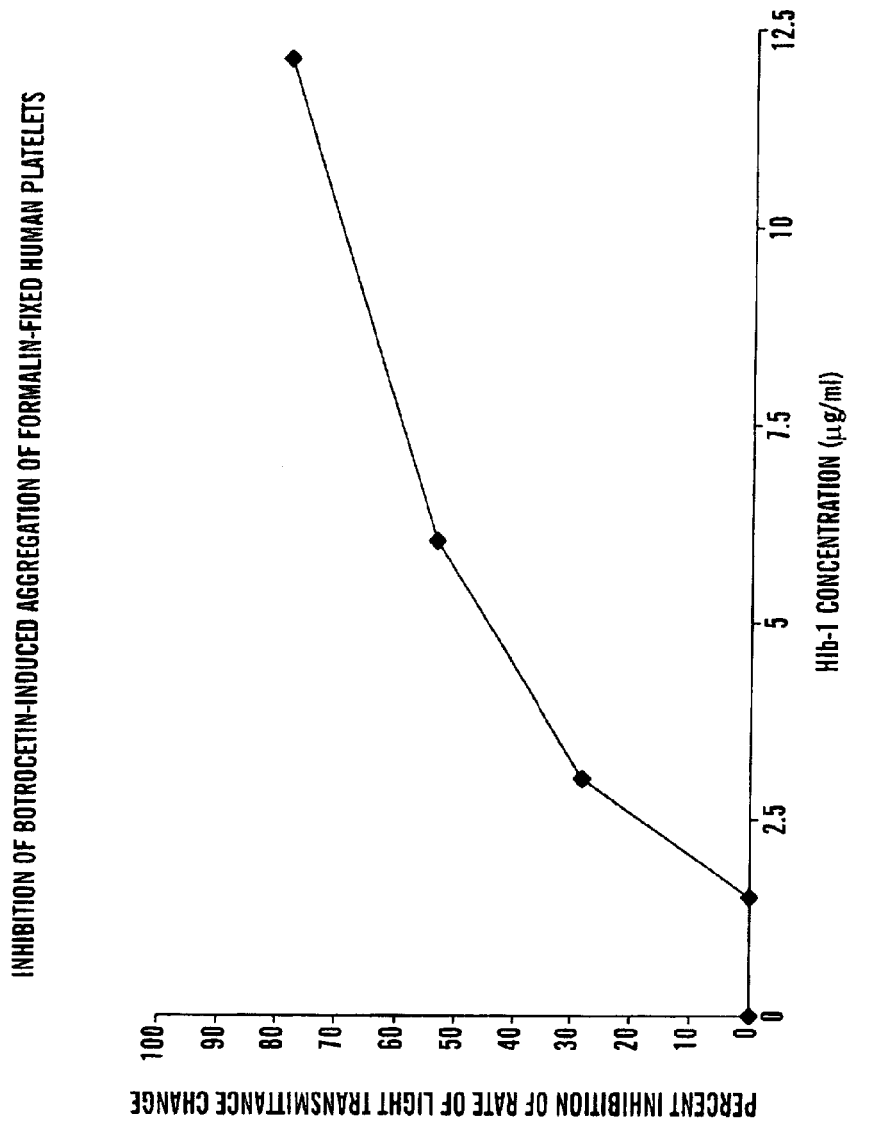
FIG. 13 illustrates inhibition of botrocetin-induced aggregation of formalin-fixed human platelets.

A representative example of inhibition at the ScFv level is shown in FIG. 13. Fixed human platelets were again used under similar conditions to those previously described. In this experiment formalin-fixed human platelets at a concentration of 150,000 µL were incubated for 1.5 hour with HIB ScFv at the indicated final concentration. Purified vWF was than added to a final concentration of 5 µg/mL, the sample put in the aggregometer in the manner described above, and botrocetin added at a final concentration of 0.6 µg/mL to initiate aggregation. In this example, the rate of light transmittance change in the aggregometer is used as an index of aggregation. Quite strong (>75%) inhibition of the aggregation response is observed when the platelets have been preincubated with 12 µg/mL HIB-1. Half-maximal inhibition is characteristically observed in the range of 5–10 µg/mL of HIb-1. Similar results are obtained when ristocetin is used as the agonist. HIB-2 ScFv similarly inhibit the aggregation of human platelets modulated by either ristocetin or botrocetin. HIB-2 ScFv also show half-maximal inhibition of such vWF-dependent platelet aggregation in the range of 5–10 µg/m ScFv, with the maximal degree of such inhibition comparable to or even exceeding that seen with HIB-1. While HIB-5 and HIB-6 also exert inhibition upon vWF-dependent platelet aggregation, the maximal degree of this inhibition has been observed to be weaker than that achieved with HIB-1 or HIB-2, reaching in the range of a 20–30% inhibition of the uninhibited aggregatory response.

Figure 14:
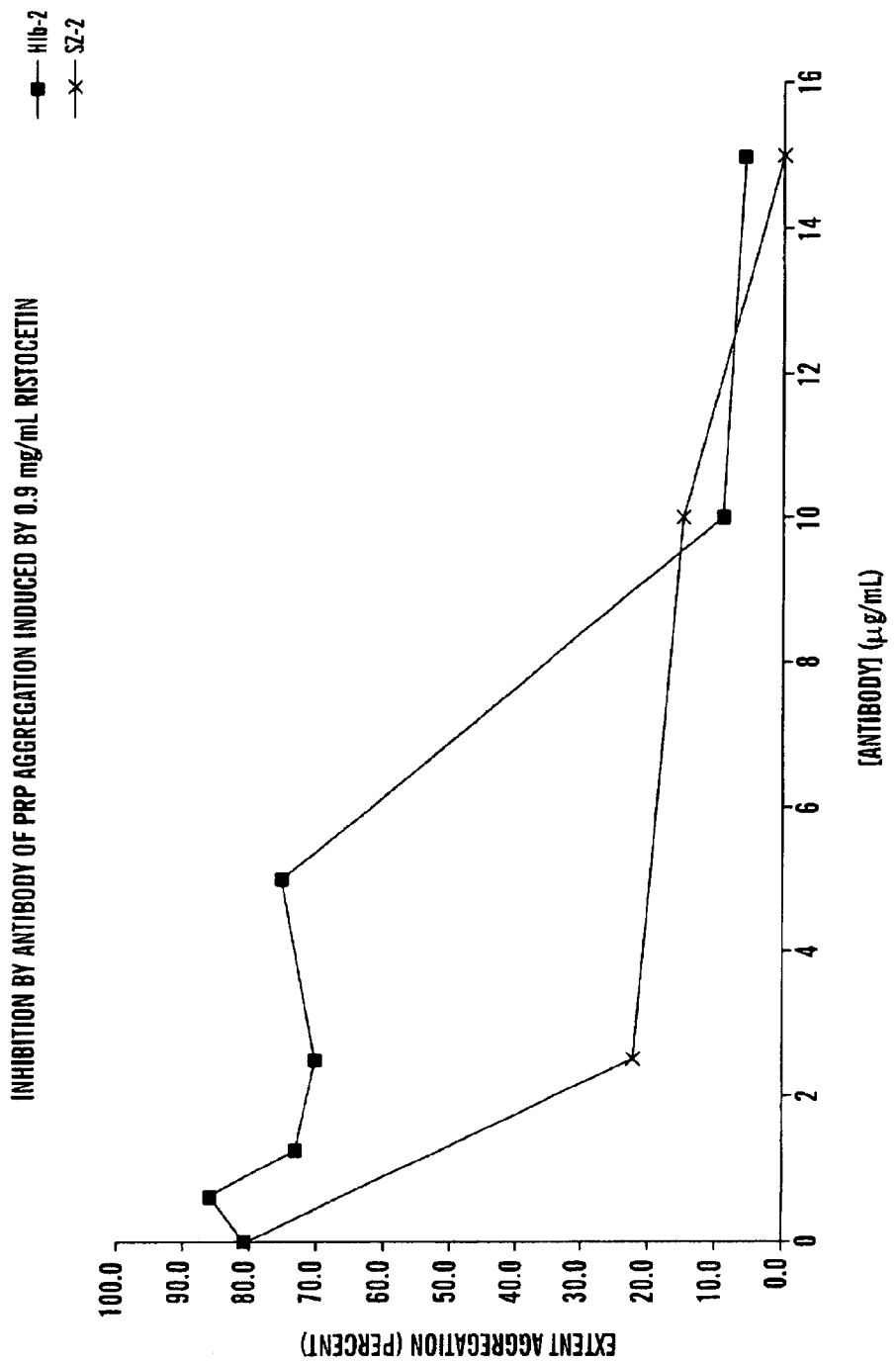
FIG. 14 illustrates inhibition of antibody by PRP aggregation induced by ristocetin.

A further representative example, in this instance demonstrating the ability of ScFv purified from the HIB clones to exert inhibitory activity upon unfixed human platelets, is shown in FIG. 14. Here the inhibitory effects of a 1 hour incubation of platelets (150,000 platelets/µL) with either HIB-2 ScFv or with the intact (i.e., full IgG) murine monoclonal antibody SZ-2 are directly compared. In this example, platelet-rich plasma (P.P.) was prepared by centrifugation of citrated, freshly drawn human blood, and the P.P. then studied in the platelet aggregometer under similar conditions as described above. It can be seen that HIB-2 by a concentration of 10 µg/mL was able to produce a degree of aggregation quite comparable to that seen with SZ-2 at the same final concentration.

This work thus demonstrates the discovery of a group of ScFv selected upon the basis of the selection strategy described above, that have been found to inhibit vWF-dependent platelet aggregation induced by botrocetin or ristocetin, and that in fact specifically recognize epitopes within human platelet GPIbα that survive SDS denaturation as well as reduction with mercaptoethanol.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES

Asfari, M., et al., Endocrinology 130:167–178 (1992).
Bayer, E. A., et al., Meth Enzym 62:308 (1979).
Bhattacharjee, A., et al., Endocrinology 138:3735–3740 (1997).
Boyd, A. E. III, *Current Concepts*, The Upjohn Company, Kalamazoo, Mich. (1991).
Campbell, A. M., *Monoclonal Antibody Technology: Laboratory Techniques in Biochemistry and Molecular Biology*, Elsevier Science Publishers, Amsterdam, The Netherlands (1984).
Capecchi, M., Cell 22:479–488 (1980).
Catterall, W. A., Science 242:50–61 (1988).
Catterall, W. A., Science 253:1499–1500 (1991).
Chomczynsk, P., et al., Anal. Biochem. 162:156–157 (1987).
Chrisey, L., et al., Antisense Research and Development 1 (1):57–63 (1991).
Christoffersen, R. E. and Marr, J. J., Journal of Medicinal Chemistry 38 (12):2023–2037 (1995).
Davalli, A. M., et al., J Endocrinology 150:195–203 (1996).
Engval, E., et al., Immunol 109:129 (1972).
Goding, J. W., J Immunol Meth 13:215 (1976).
Han, L., et al., Proc Natl Acad Sci USA 88:4313–4317 (1991).
Hiriart, M. and Matteson, D. R., J Gen Physiol 91:145–159 (1988).
Innis, et al., *PCR Protocols*, Academic Press, San Diego, Calif. (1990).
Kato, S., et al., Metabolism 43:1395–1400 (1994).
Kato, S., et al., J Clin Invest 97:2417–2425 (1996).
Keahey, H. H., et al., Diabetes 38:188–193 (1989).
Klein, T. M., et al., Nature 327:70–73 (1987).
Lutz, et al., Exp Cell Res 175:109–124 (1988).
Mannino, R. J. and Gould-Fogerite, S., BioTechniques 6:682–690 (1988).
Miller, L. K., Bioessays 11:91–95 (1989).
Perez-Reyes, E., et al., Nature 391:896–900 (1998).
Rossi, J. J., et al., AIDS Research and Human Retroviruses 8(2):183–189 (1992).
Rossi, J. J., British Medical Bulletin 51 (1):217–225 (1995).
Sambrook et al., *Molecular Cloning: A Laboratory Manual*, 2d Edition, Cold Spring Harbor Laboratory Press, Cold Spring Harbor, N.Y. (1989).
Sarver, N., et al., Science 247:1222–1225 (1990).
Seino, S., et al., Proc Natl Acad Sci USA 89:584–588 (1992).
Shigekawa, K. and Dower, W. J., BioTechniques 6:742–751 (1988).
Stea, A., et al., In: Ligand and voltage-gated ion channels. pp113–151, ed. R. Alan North, CRC Press, Boca Raton (1995).
Sternberger, L. A., et al., J Histochem Cytochem 18:315 (1970).
St. Groth, et al., J Immunol Methods 35:1–21 (1980).
Vague, P. and Moulin, J. P., Metabolism 31:139–144 (1982).
Wiltshire, H. R., et al., Xenobiotica 22:837–857 (1992).
Wang, L., et al., Diabetes 45:1678–1683 (1996).
Yaney, G. C., et al., Mol Endocrinol 6:2143–2152 (1992).
Hoogenboom and Winter, J Mol Biol 222:381–388 (1992).
Vaughan et al., Nature Biotech 14:309–315 (1996).
McCafferty et al., Nature 348(6301):552–554 (1990).
Tomlinson et al., J Mol Biol 227:776–798 (1992).
Nissim et al., EMBO J. 13(3):692–698 (1994).
Griffiths et al., EMBO J. 13(14):3245–3260 (1994).
Hiraiwa et al., Autoimmunity 8:107–113 (1990).

Balass, M. et al., Proc Natl Acad Sci USA 90:10638–10642 (November 1993).
Becker, B. H. and Miller, J. L., Blood 74:690–694 (1989).
Chambers, M. et al., in *Leucocyte Typing V: White Cell Differentiation Antigens*, ed. Schlossman, S., pp. 1343–1345, Oxford University Press, New York (1995).
Christian, R. B. et al., J Mol Biol 227:711–718 (1992).
Clemetson, K. J. and Clemetson, J. M., Sem. Thromb. Hemost. 21:130–136 (1995).
Clemetson, K. J. and Hugli, B., in *Leucocyte Typing V: White Cell Differentiation Antigens*, ed. Schlossman, S., pp. 1323–1325 Oxford University Press, New York (1995).
Cwirla, S. E. et al., Proc Natl Acad Sci USA 87:6378–6382 (August 1990).
Devlin, J. J. et al., Science 249:404–406 (1990).
Du, X. et al., Blood 69:1524–1527 (1987).
Fitzgerald, L. A. and Phillips, D. R., in *Platelet Immunobiology: Molecular and Clinical Aspects*, Kunicki, T. J. and George, J. N., Eds., pp. 9–30, Lippincott, Philadelphia Pa. (1989).
Fox, J. E. B. et al., J. Biol Chem 263:4882–4890 (1988).
Hobart, M. J. et al., Proc R Soc London B 252:157–162 (1993).
Joyce, G. F., Current Opinion in Structural Biology 4:331–336 (1994).
Kupinski, J. M. and Miller, J. L., Thromb Res 43:335–344 (1986).
LaRocca, D. et al., Hybridoma 11:191–201 (1992).
Lenstra, J. A. et al., J Immunol Methods 152:149–157 (1992).
Lopez, J. A., Blood Coag. & Fibrinolysis 5:97–119 (1994).
Luzzago, A. et al., Gene 128:51–57 (1993).
Macfarlane, D. E., et al. Thrombos Diath Haemorrh 34:306–308 (1975).
Miller, J. L. and Castella, A., Blood 60:790–794 (1982).
Miller, J. L. et al., J Clin Invest 72:1532–1542 (1983).
Miller, J. L. et al., Blood 68:743–751 (1986).
Miller, J. L. et al., Blood 70:1804–1809 (1987).
Miller, J. L. et al., Br J Haemotol 74:313–319 (1990).
Miller, J. L. et al., Proc Natl Acad Sci USA 88:4761–4765 (1991).
Miller, J. L. et al., Blood 79:439–446 (1992).
Molino, M. et al., Blood 82:2442–2451 (1993).
Motti, C. et al., Gene 146:191–198 (1994).
Murata, M., et al., J Clin Invest 92:1555–1558 (1993).
Parmley, S. F. and Smith, G. P., Gene 73:305–318 (1988).
Pearson, W. R. and Lipman, D. J., Proc Natl Acad Sci USA 85:2444–2448 (1988).
Pearson, W. R., Methods in Enzymology 183:63–98 (1990).
Roth, G. J., Blood 77:5–19 (1991).
Ruan, C. et al., Blood 69:570–577 (1987).
Russell, S. D. and Roth, G. J., Blood 81:1787–1791 (1993).
Scott, J. K., Trends in Biochem Sci 17:241–245 (1992).
Scott, J. K. and Smith, G. P., Science 249:386–390 (Jul. 27, 1990).
Smith, G. P. and Scott, J. K., Methods in Enzymology 217:228–257 (1993).
Takahashi, H. et al., Thromb Res 19:857–867 (1980).
Takahashi, H. et al., Blood 85:727–733 (1995).
Ward, C. M. and Berndt, M. C., in *Leucocyte Typing V: White Cell Differentiation Antigens*, ed. Schlossman, S., pp. 1336–1337, Oxford University Press, New York (1995).
Weiss, H. J. et al., N Engl J Med 306:326–362 (1982).

What is claimed is:

1. An isolated variable heavy chain region of an antibody, wherein the antibody binds to human platelet glycoprotein Ib alpha and inhibits aggregation of platelets wherein the variable heavy chain region has a first amino acid sequence having at least 95% amino acid identity to a second amino acid sequence and the second amino acid sequence is selected from the group consisting of SEQ ID NO 10, SEQ ID NO 14 and SEQ ID NO 62.

2. An isolated variable heavy chain region of an antibody, wherein the variable heavy chain region has an amino acid sequence selected from the group consisting of SEQ ID NO 10, SEQ ID NO 14 and SEQ ID NO 62.

3. An antibody comprising the variable heavy chain region of claim 1 or 2.

4. The antibody of claim 3 wherein the antibody is monovalent.

5. The antibody of claim 3 wherein the antibody is bivalent.

6. The antibody of claim 3 wherein the antibody is polyvalent.

7. A composition comprising the antibody of claim 3 and a carrier.

* * * * *